US012606637B2

(12) United States Patent
Vlodavsky et al.

(10) Patent No.: US 12,606,637 B2
(45) Date of Patent: Apr. 21, 2026

(54) HEPARANASE-NEUTRALIZING A54 MONOCLONAL ANTIBODY

(71) Applicants: TECHNION RESEARCH & DEVELOPMENT FOUNDATION LIMITED, Haifa (IL); HADASIT MEDICAL RESEARCH SERVICES AND DEVELOPMENT LTD., Jerusalem (IL)

(72) Inventors: Israel Vlodavsky, Mevasseret Zion (IL); Uri Barash, Haifa (IL)

(73) Assignees: TECHNION RESEARCH & DEVELOPMENT FOUNDATION LIMITED, Haifa (IL); HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 646 days.

(21) Appl. No.: 18/014,530

(22) PCT Filed: Jul. 6, 2021

(86) PCT No.: PCT/IL2021/050830
§ 371 (c)(1),
(2) Date: Jan. 5, 2023

(87) PCT Pub. No.: WO2022/009203
PCT Pub. Date: Jan. 13, 2022

(65) Prior Publication Data
US 2023/0265213 A1     Aug. 24, 2023

Related U.S. Application Data

(60) Provisional application No. 63/048,211, filed on Jul. 6, 2020.

(51) Int. Cl.
| | |
|---|---|
| A61K 39/395 | (2006.01) |
| A61K 31/69 | (2006.01) |
| A61K 31/7068 | (2006.01) |
| A61P 35/00 | (2006.01) |
| A61P 35/04 | (2006.01) |
| C07K 16/40 | (2006.01) |
| A61K 39/00 | (2006.01) |

(52) U.S. Cl.
CPC .............. *C07K 16/40* (2013.01); *A61K 31/69* (2013.01); *A61K 31/7068* (2013.01); *A61K 39/3955* (2013.01); *A61P 35/00* (2018.01); *A61P 35/04* (2018.01); *A61K 2039/505* (2013.01); *C07K 2317/565* (2013.01); *C07K 2317/76* (2013.01)

(58) Field of Classification Search
CPC .............. C07K 16/40; C07K 2317/565; C07K 2317/76; A61P 35/04; A61P 35/00; A61K 31/69; A61K 31/7068; A61K 39/3955; A61K 2039/505
See application file for complete search history.

(56) References Cited

U.S. PATENT DOCUMENTS

| | | |
|---|---|---|
| 4,816,567 A | 3/1989 | Cabilly et al. |
| 4,946,778 A | 8/1990 | Ladner et al. |
| 5,091,513 A | 2/1992 | Huston et al. |
| 5,096,815 A | 3/1992 | Ladner et al. |
| 5,225,539 A | 7/1993 | Winter |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,591,828 A | 1/1997 | Bosslet et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,693,761 A | 12/1997 | Queen et al. |
| 5,693,762 A | 12/1997 | Queen et al. |
| 5,750,373 A | 5/1998 | Garrard et al. |
| 6,177,545 B1 | 1/2001 | Pecker et al. |

(Continued)

FOREIGN PATENT DOCUMENTS

| | | |
|---|---|---|
| EP | 0404097 | 12/1990 |
| WO | WO 1986/001533 | 3/1986 |

(Continued)

OTHER PUBLICATIONS

Garsen_et_al_Journal_of_Pathology_2015_vol. 237_pp. 472-481 (Year: 2015).*
SCV_Result_for_Instant_SEQ_ID_NO_5_for_Osterroth_et_al (Year: 2018).*
U.S. Appl. No. 08/256,790, filed Jul. 22, 1994, Plickthun, Andreas., et al..
U.S. Appl. No. 08/817,788, filed Sep. 12, 1997, Gan, Joseph., et al..
Abassi, Zaid, and M. S. Goligorsky. "Heparanase in acute kidney injury." Heparanase: From Basic Research to Clinical Applications (2020): 685-702.
Agelidis, Alex, and Deepak Shukla. "Heparanase, heparan sulfate and viral infection." Heparanase: From Basic Research to Clinical Applications (2020): 759-770.

(Continued)

*Primary Examiner* — Catherine S Hibbert
(74) *Attorney, Agent, or Firm* — PEARL COHEN ZEDEK LATZER BARATZ LLP

(57) ABSTRACT

The present invention relates to an heparanase-binding and heparanase-neutralizing monoclonal antibody (IgG-1 mAb A54), including its epitope (HBD-II) and mode of interaction with heparanase, pharmaceutical composition comprising same, and uses thereof e.g. for inhibiting or treating a disease or disorder associated with heparanase activity, including but not limited to cancer, inflammation, viral infection, diabetes and related complications. The present invention further provides combinatorial cancer therapies, comprising the heparanase-neutralizing mAb and an additional anti-cancer treatment such as chemotherapy or radiation.

4 Claims, 25 Drawing Sheets

Specification includes a Sequence Listing.

(56) References Cited

U.S. PATENT DOCUMENTS

| | | | |
|---|---|---|---|
| 6,190,875 | B1 | 2/2001 | Ben-Artzi et al. |
| 6,562,950 | B2 | 5/2003 | Peretz et al. |
| 7,772,187 | B2 | 8/2010 | Vlodavsky et al. |
| 8,048,993 | B2 | 11/2011 | Pecker et al. |
| 9,995,733 | B2 * | 6/2018 | Osterroth ................ A61P 37/06 |

FOREIGN PATENT DOCUMENTS

| | | |
|---|---|---|
| WO | WO 1990/007861 | 7/1990 |
| WO | WO 1992/022653 | 12/1992 |
| WO | WO 1993/011161 | 6/1993 |
| WO | WO 1993/015210 | 8/1993 |
| WO | WO 1996/013583 | 5/1996 |
| WO | WO 1996/037621 | 11/1996 |
| WO | WO 1997/002671 | 1/1997 |
| WO | WO 2003/012105 | 2/2003 |
| WO | WO 2004/108065 | 12/2004 |
| WO | WO 2010/041060 | 4/2010 |
| WO | WO 2017/064716 | 4/2017 |

OTHER PUBLICATIONS

Arvatz G, Barash U, Nativ O, Ilan N, Vlodavsky I. Post-transcriptional regulation of heparanase gene expression by a 3' AU-rich element. Faseb J. Dec. 2010;24(12):4969-76.

Barash, Uri, et al. "A novel human heparanase splice variant, T5, endowed with protumorigenic characteristics." The FASEB Journal 24.4 (2010): 1239.

Barash, Uri, et al. "Heparanase promotes glioma progression via enhancing CD24 expression." International journal of cancer 145.6 (2019): 1596-1608.

Barash, Uri, et al. "Involvement of heparanase in the pathogenesis of mesothelioma: basic aspects and clinical applications." JNCI: Journal of the National Cancer Institute 110.10 (2018): 1102-1114.

Bird, Robert E., et al. "Single-chain antigen-binding proteins." Science 242.4877 (1988): 423-426.

Boerner, Paula, et al. "Production of antigen-specific human monoclonal antibodies from in vitro-primed human splenocytes." Journal of immunology (Baltimore, Md.: 1950) 147.1 (1991): 86-95.

Campbell, Julie H., et al. "Heparan sulfate-degrading enzymes induce modulation of smooth muscle phenotype." Experimental cell research 200.1 (1992): 156-167.

Casset, Florence, et al. "A peptide mimetic of an anti-CD4 monoclonal antibody by rational design." Biochemical and biophysical research communications 307.1 (2003): 198-205.

Casu et al., "Non-Anticoagulant Heparins and Inhibition of Cancer", Pathophysiology of Haemostasis and Thrombosis, 2008, 36(3-4), pp. 195-203.

Chen, Yvonne, et al. "Selection and analysis of an optimized anti-VEGF antibody: crystal structure of an affinity-matured Fab in complex with antigen." Journal of molecular biology 293.4 (1999): 865-881.

Chhabra, Mohit, and Vito Ferro. "PI-88 and Related Heparan Sulfate Mimetic s." Heparanase: From basic research to clinical applications (2020): 473-491.

Clackson, Tim, et al. "Making antibody fragments using phage display libraries." Nature 352.6336 (1991): 624-628.

Cole, S. P. C. "Monoclonal Antibodies and Cancer Therapy, Alan R. Liss." Inc., New York, New York (1985): 77-96.

De Pascalis, Roberto, et al. "Grafting of "abbreviated" complementarity-determining regions containing specificity-determining residues essential for ligand contact to engineer a less immunogenic humanized monoclonal antibody." The Journal of Immunology 169.6 (2002): 3076-3084.

Dredge et al., "PG545, a dual heparanase and angiogenesis inhibitor, induces potent anti-tumour and anti-metastatic efficacy in preclinical models", British Journal of Cancer (2011) 104(4), 635-642.

Edovitsky, Evgeny, et al. "Role of endothelial heparanase in delayed-type hypersensitivity." Blood 107.9 (2006): 3609-3616.

Fishwild, Dianne M., et al. "High-avidity human IgGK monoclonal antibodies from a novel strain of minilocus transgenic mice." Nature biotechnology 14.7 (1996): 845-851.

Galanis et al. "Bacteriophage Library Construction and Selection of Recombinant Antibodies", Current Protocols in Immunology, Chapter 17:1.1.1.-17:1.1.48, May 2001.

Giannini, Giuseppe, Gianfranco Battistuzzi, and Silvia Rivara. "The control of heparanase through the use of small molecules." Heparanase: From Basic Research to Clinical Applications (2020): 567-603.

Gil et al., "Heparanase Is Essential for the Development of Diabetic Nephropathy in Mice", Diabetes, Jan. 2012; vol. 61, pp. 208-216.

Gingis-Velitski S, Ishai-Michaeli R, Vlodavsky I, Ilan N. Anti-heparanase monoclonal antibody enhances heparanase enzymatic activity and facilitates wound healing. FASEB J. Dec. 2007;21(14):3986-93.

Hammond, Edward, and Keith Dredge. "Heparanase inhibition by pixatimod (PG545): basic aspects and future perspectives." Heparanase: From Basic Research to Clinical Applications (2020): 539-565.

Hammond, Edward, Ralf Brandt, and Keith Dredge. "PG545, a heparan sulfate mimetic, reduces heparanase expression in vivo, blocks spontaneous metastases and enhances overall survival in the 4T1 breast carcinoma model." PloS one 7.12 (2012): e52175.

He et al., Hypoxia Increases Heparanase-Dependent Tumor Cell Invasion, Which Can BeInhibited by Antiheparanase Antibodies, Cancer Research, Jun. 1, 2004, 64( 11), pp. 3928-3933.

Holliger P, Prospero T, Winter G. "Diabodies": small bivalent and bispecific antibody fragments. Proc Natl Acad Sci U S A. Jul. 15, 1993;90(14):6444-8.

Hoogenboom, Hennie R., and Greg Winter. "By-passing immunisation: human antibodies from synthetic repertoires of germline VH gene segments rearranged in vitro." Journal of molecular biology 227.2 (1992): 381-388.

Huston, James S., et al. "Protein engineering of antibody binding sites: recovery of specific activity in an anti-digoxin single-chain Fv analogue produced in Escherichia coli." Proceedings of the National Academy of Sciences 85.16 (1988): 5879-5883.

Jones, Peter T., et al. "Replacing the complementarity-determining regions in a human antibody with those from a mouse." Nature 321.6069 (1986): 522-525.

Katz et al.,"Involvement of Human Heparanase in the Pathogenesis of Diabetic Nephropathy", Isr. Med. Assoc. Nov. 2002, vol. 4, pp. 996-1002.

Khamaysi, Iyad, Dalit B. Hamo-Giladi, and Zaid Abassi. "Heparanase in acute pancreatitis." Heparanase: From Basic Research to Clinical Applications (2020): 703-719.

Kohler, Georges, and Cesar Milstein. "Continuous cultures of fused cells secreting antibody of predefined specificity." nature 256.5517 (1975): 495-497.

Kozbor, Danuta, and John C. Roder. "The production of monoclonal antibodies from human lymphocytes." Immunology Today 4.3 (1983): 72-79.

Lamminmaki, Urpo, and Jussi A. Kankare. "Crystal structure of a recombinant anti-estradiol Fab fragment in complex with 17ß-estradiol." Journal of Biological Chemistry 276.39 (2001): 36687-36694.

Lerner et al., "Heparanase powers a chronic inflammatory circuit that promotes colitis-associated tumorigenesis in mice", May 2011, The Journal of Clinical Investigation, vol. 121, No. 5, pp. 1709-1721.

Levidiotis et al., "Heparanase inhibition reduces proteinuria in a model of accelerated anti-glomerular basement membrane antibody disease", 2005 Asian Pacific Society of Nephrology, vol. 10, No. 2, pp. 167-173.

Levidiotis et al., "Increased expression of heparanase in puromycin aminonucleoside nephrosis", Kidney International, vol. 60 (2001), pp. 1287-1296.

Levidiotis, Vicki, et al. "Heparanase is involved in the pathogenesis of proteinuria as a result of glomerulonephritis." Journal of the American Society of Nephrology 15.1 (2004): 68-78.

Levy-Adam et al. "Identification and Characterization of Heparin/Heparan Sulfate Binding Domains of the Endoglycosidase Heparanase", The Journal of Biological Chemistry, vol. 280, No. 21, May 27, 2005, pp. 20457-20466.

(56)          References Cited

OTHER PUBLICATIONS

Levy-Adam, Flonia, et al. "Heparanase 2 interacts with heparan sulfate with high affinity and inhibits heparanase activity." Journal of Biological Chemistry 285.36 (2010): 28010-28019.

Li, Jin-Ping, and Xiao Zhang. "Implications of heparan sulfate and heparanase in amyloid diseases." Heparanase: From Basic Research to Clinical Applications (2020): 631-645.

Li, Rachel W., et al. "Dramatic regulation of heparanase activity and angiogenesis gene expression in synovium from patients with rheumatoid arthritis." Arthritis & Rheumatism: Official Journal of the American College of Rheumatology 58.6 (2008): 1590-1600.

Lloyd, C., et al. "Modelling the human immune response: performance of a 1011 human antibody repertoire against a broad panel of therapeutically relevant antigens." Protein Engineering, Design & Selection 22.3 (2009): 159-168.

Lonberg, Nils, and Dennis Huszar. "Human antibodies from transgenic mice." International reviews of immunology 13.1 (1995): 65-93.

Lonberg, Nils, et al. "Antigen-specific human antibodies from mice comprising four distinct genetic modifications." Nature 368.6474 (1994): 856-859.

MacCallum, Robert M., Andrew CR Martin, and Janet M. Thornton. "Antibody-antigen interactions: contact analysis and binding site topography." Journal of molecular biology 262.5 (1996): 732-745.

Marks, James D., et al. "By-passing immunization: building high affinity human antibodies by chain shuffling." Bio/technology 10.7 (1992): 779-783.

Marks, James D., et al. "By-passing immunization: human antibodies from V-gene libraries displayed on phage." Journal of molecular biology 222.3 (1991): 581-597.

Masola, Valentina, Giovanni Gambaro, and Maurizio Onisto. "Impact of heparanse on organ fibrosis." Heparanase: From Basic Research to Clinical Applications (2020): 669-684.

Morrison, Sherie L. "Success in specification." Nature 368.6474 (1994).

Morrison, Sherie L., et al. "Chimeric human antibody molecules: mouse antigen-binding domains with human constant region domains." Proceedings of the National Academy of Sciences 81.21 (1984): 6851-6855.

Myler et al., "Novel Heparanase-Inhibiting Antibody Reduces Neointima Formation", 2006 The Japanese Biochemical Society, vol. 139, No. 3, pp. 339-345.

Naggi et al., "Modulation of the Heparanase-inhibiting Activity of Heparin through Selective Desulfation, Graded N-Acetylation, and Glycol Splitting", The Journal of Biological Chemistry 2005, vol. 280, No. 13, pp. 12103-12113.

Neuberger, Michael. "Generating high-avidity human Mabs in mice." Nature biotechnology 14.7 (1996): 826-826.

Noseda, Alessandro, and Paola Barbieri. "Roneparstat: development, preclinical and clinical studies." Heparanase: From Basic Research to Clinical Applications (2020): 523-538.

Padlan, Eduardo A., et al. "Structure of an antibody-antigen complex: crystal structure of the HyHEL-10 Fab-lysozyme complex." Proceedings of the National Academy of Sciences 86.15 (1989): 5938-5942.

Piche-Nicholas, Nicole M., et al. "Changes in complementarity-determining regions significantly alter IgG binding to the neonatal Fc receptor (FcRn) and pharmacokinetics." MAbs. Vol. 10. No. 1. Taylor & Francis, 2018.

Planer, David, et al. "Role of heparanase on hepatic uptake of intestinal derived lipoprotein and fatty streak formation in mice." PloS one 6.4 (2011): e18370.

Presta, Leonard G. "Antibody engineering." Current Opinion in Structural Biology 2.4 (1992): 593-596.

Ramani, Vishnu C., et al. "Chemotherapy induces expression and release of heparanase leading to changes associated with an aggressive tumor phenotype." Matrix biology 55 (2016): 22-34.

Riechmann, Lutz, et al. "Reshaping human antibodies for therapy." Nature 332.6162 (1988): 323-327.

Ritchie et al., "SST0001, a Chemically Modified Heparin, Inhibits Myeloma Growth and Angiogenesis via Disruption of the Heparanase/Syndecan-1 Axis", Mar. 15, 2011, Clinical Cancer Research; vol. 17, No. 6, pp. 1382-1393.

Rudikoff, Stuart, et al. "Single amino acid substitution altering antigen-binding specificity." Proceedings of the National Academy of Sciences 79.6 (1982): 1979-1983.

Schroeder Jr, Harry W., and Lisa Cavacini. "Structure and function of immunoglobulins." Journal of allergy and clinical immunology 125.2 (2010): S41-S52.

Shafat, Itay, et al. "An ELISA method for the detection and quantification of human heparanase." Biochemical and biophysical research communications 341.4 (2006): 958-963.

Shang, Rui, et al. "Involvement of heparanase in endothelial cell-cardiomyocyte crosstalk." Heparanase: From Basic Research to Clinical Applications (2020): 721-745.

Sheets, Michael D., et al. "Efficient construction of a large nonimmune phage antibody library : the production of high-affinity human single-chain antibodies to protein antigens." Proceedings of the National Academy of Sciences 95.11 (1998): 6157-6162.

Simeonovic, Charmaine J., et al. "Heparanase and type 1 diabetes." Heparanase: From Basic Research to Clinical Applications (2020): 607-630.

Vajdos, Felix F., et al. "Comprehensive functional maps of the antigen-binding site of an anti-ErbB2 antibody obtained with shotgun scanning mutagenesis." Journal of molecular biology 320.2 (2002): 415-428.

van der Vlag, J. and Buijsers, B., 2020. Heparanase in kidney disease (pp. 647-667). Springer International Publishing.

Vaughan, Tristan J., et al. "Human antibodies with sub-nanomolar affinities isolated from a large non-immunized phage display library." Nature biotechnology 14.3 (1996): 309-314.

Vlodavsky et al. "Expression of Heparanase by Platelets and Circulating Cells of the Immune System: Possible Involvement in Diapedeses and Extravasation", Invasion & Metastasis, 12: 112-127, 1992.

Vlodavsky I. Preparation of extracellular matrices produced by cultured corneal endothelial and PF-HR9 endodermal cells. Curr Protoc Cell Biol. May 2001;Chapter 10: Unit 10.4.

Vlodavsky, Israel, et al. "Mammalian heparanase: gene cloning, expression and function in tumor progression and metastasis." Nature medicine 5.7 (1999): 793-802.

Ward, E. Sally, et al. "Binding activities of a repertoire of single immunoglobulin variable domains secreted from *Escherichia coli*." Nature 341.6242 (1989): 544-546.

Wu, Herren, et al. "Humanization of a murine monoclonal antibody by simultaneous optimization of framework and CDR residues." Journal of Molecular Biology 294.1 (1999): 151-162.

Xiao et al., Heparanase expression in hepatocellular carcinoma and the cirrhotic liver, Hepatology Research, Jul. 2003; 26(3):192-198.

Yang et al., " The syndecan-1 heparan sulfate proteoglycan is a viable target for myeloma therapy", Blood. Sep. 15, 2007; vol. 110, No. 6, pp. 2041-2048.

Zapata, Gerardo, et al. "Engineering linear F (ab') 2 fragments for efficient production in *Escherichia coli* and enhanced antiproliferative activity." Protein Engineering, Design and Selection 8.10 (1995): 1057-1062.

Zetser et al., " Processing and activation of latent heparanase occurs in lysosomes", Journal of Cell Science, 2004, vol. 117, No. 11, pp. 2249-2258.

Ziolkowski et al., "Heparan sulfate and heparanase play key roles in mouse b cell survival and autoimmune diabetes", The Journal of Clinical Investigation Jan. 2012; vol. 122, No. 1, pp. 132-141.

Schroeder et al: "Structure and function of immunoglbulins", J Allergy Clin Immunol 2010. Vol 125 : pp. S41-S52.

Lloyd et al: "Modelling the human immune response: performance of a 1011 human antibody repertoire against a broad panel of therapeutically relevant antigens"; Protein Engineering, Design & Selection vol. 22 No. 3 pp. 159-168, 2009; Published online Oct. 29, 2008 doi:10.1093/protein/gzn058.

Rudikoff et al: "Single amino acid substitution altering antigen-binding specificity"; Proc. Nat. Acad. Sci. USA, vol. 79, pp. 1979-1983, Mar. 1982, Immunology.

(56)  References Cited

OTHER PUBLICATIONS

MacCallum et al: "Antibody-antigen Interactions: Contact Analysis and Binding Site Topography"; Journal of Molecular Biology; vol. 262, Issue 5, Oct. 11, 1996, pp. 732-745.

Pascalis et al: "Grafting of Abbreviated Complementarity-Determining Regions Containing Specificity-Determining Residues Essential for Ligand Contact to Engineer a Less Immunogenic Humanized Monoclonal Antibody"; Journal of Immunology; Research Article; Published Sep. 15, 2002; J Immunol (2002) 169 (6): 3076-3084.

Casset et al: "A peptide mimetic of an anti-CD4 monoclonal antibody by rational design"; Biochemical and Biophysical Research Communications; 307 (2003) pp. 198-205; published May 20, 2003.

Vajdos et al: "Comprehensive Functional Maps of the Antigen binding Site of an Anti-ErbB2 Antibody Obtained with Shotgun Scanning Mutagenesis"; Journal of Molecular Biology; J. Mol Biol (2002) 320, pp. 415-428; published Jan. 14, 2002.

Chen et al: "Selection and Analysis of an Optimized Anti-VEGF Antibody: Crystal Structure of an Affinity-matured Fab in Complex with Antigen"; Journal of Molecular Biology; J. Mol Biol (1999) 293, pp. 865-881; published Jul. 19, 1999.

Wu et al: "Humanization of a Murine Monoclonal Antibody by Simultaneous Optimization of Framework and CDR Residues"; Journal of Molecular Biology; J. Mol Biol (1999) 294, pp. 151-162; published May 11, 1999.

Padlan et al: "Structure of an antibody-antigen complex: Crystal structure of the HyHEL-10 Fab-lysozyme complex"; Proc. Natl. Academy of Science, USA; vol. 86, pp. 5938-5942; published Aug. 1989.

Lamminmaki et al: "Crystal Structure of a Recombinant Anti-estradiol Fab Fragment in Complex with 17-Estradiol*" The Journal of Biological Chemistry vol. 276, No. 39, Issue of Sep. 28, pp. 36687-36694, 2001; Published Mar. 16, 2001.

Piche Nicholas et al: "Changes in complementarity-determining regions significantly alter IgG binding to the neonatal Fc receptor (FcRn) and pharmacokinetics"; published online Nov. 3, 2017; https://doi.org/10.1080/19420862.2017.1389355.

Marina Weissmann et al: "Heparanase-neutralizing antibodies attenuate lymphoma tumor growth and metastasis", Proceedings of the National Academy of Sciences, vol. 113, No. 3, Jan. 19, 2016, ,pp. 704-709, XP055568232.

Mathieu Dondelinger et al: "Understanding the Significance and Implications of Antibody Numbering and Antigen-Binding Surface / Residue Definition", Frontiers in Immunology, vol. 9, Oct. 16, 2018, pp. 1-15, ZP055572450.

Inbal Sela-Culag et al: "The Structural Basis of Antibody-Antigen Recognition", Frontiers in Immunology, vol. 4, Oct. 8, 2013, XP055557261.

Honegger A: "Engineering antibodies for stability and efficient folding",Dec. 31, 2008; XP093032606; DOI: 10.1007/978-3-540-73259-4.

* cited by examiner

SDS-PAGE

Western Blot

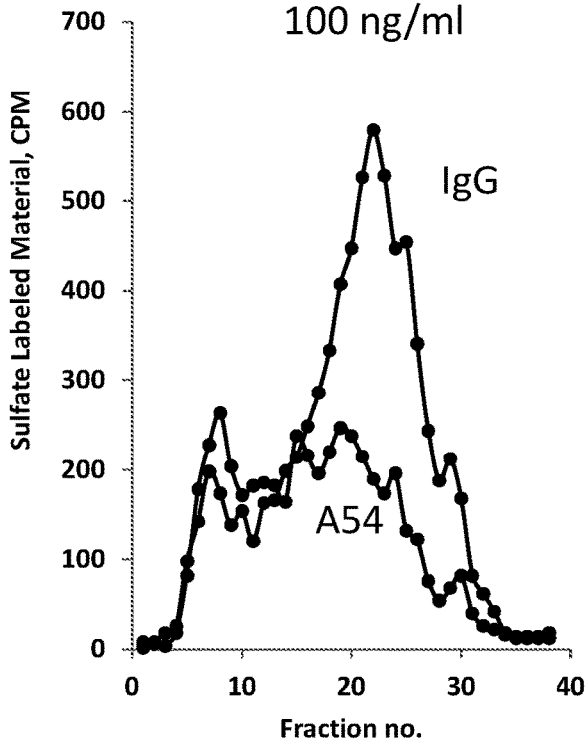
Figure 3B
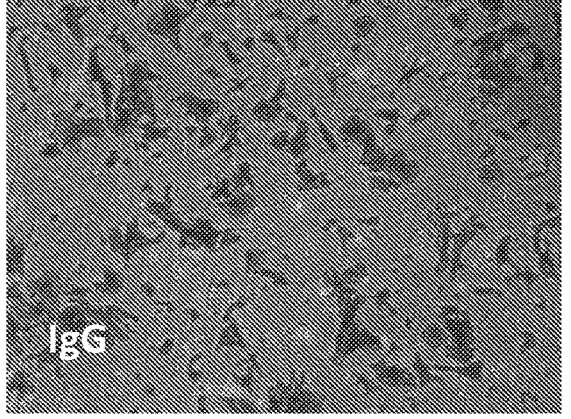
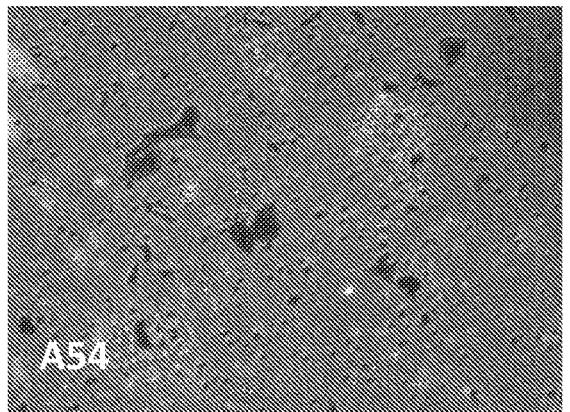
Figure 4A                                              Figure 4B

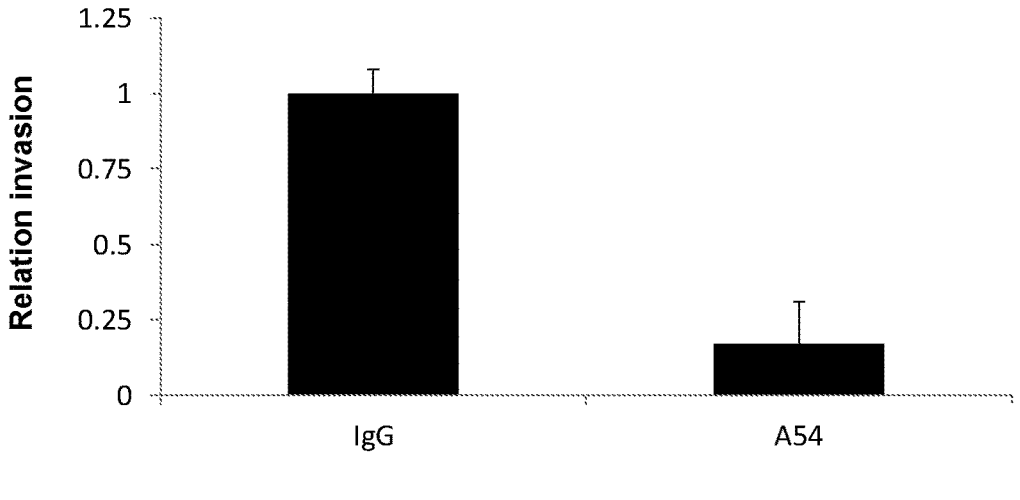
Figure 4C
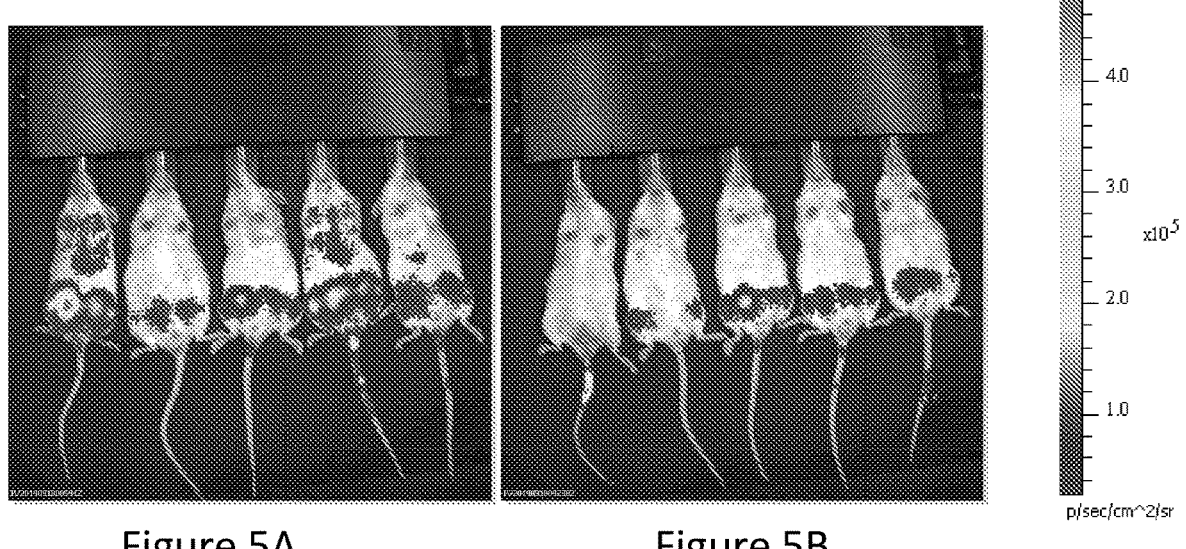
Figure 5A                    Figure 5B

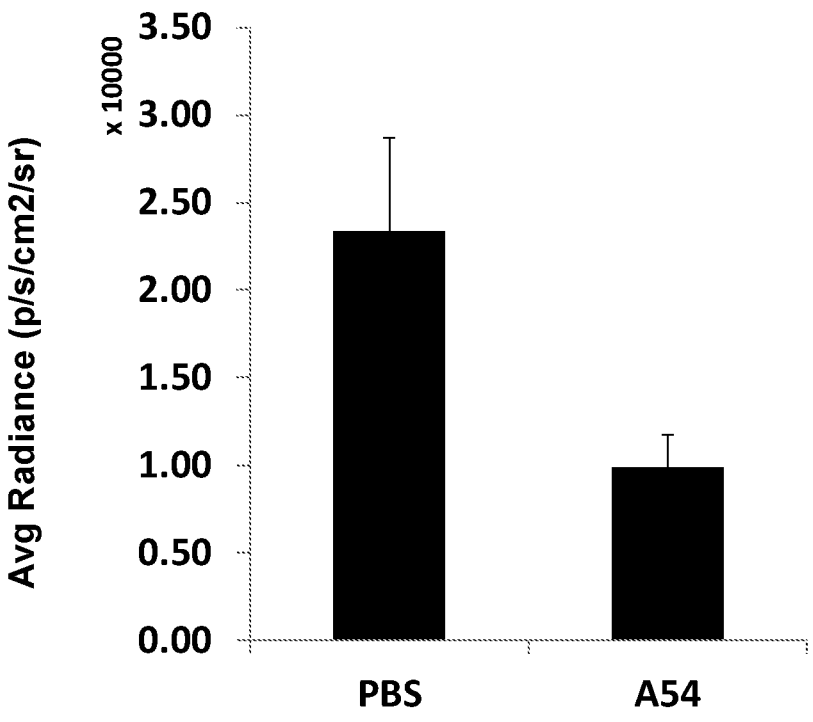
Figure 5C
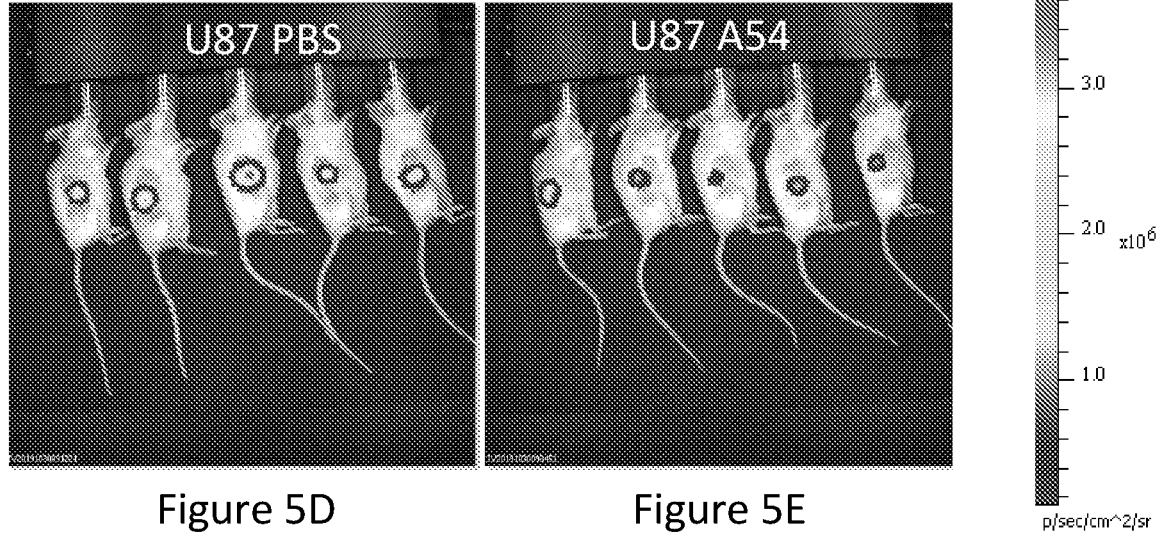
Figure 5D                    Figure 5E

PBS
A54 500                                    X
A54 250
Figure 6C
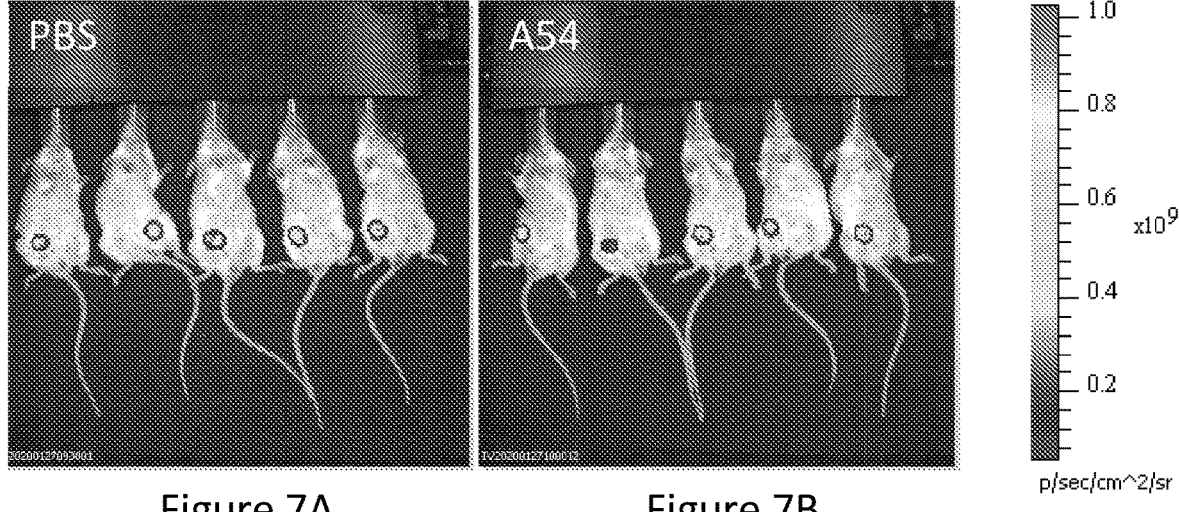
Figure 7A                              Figure 7B

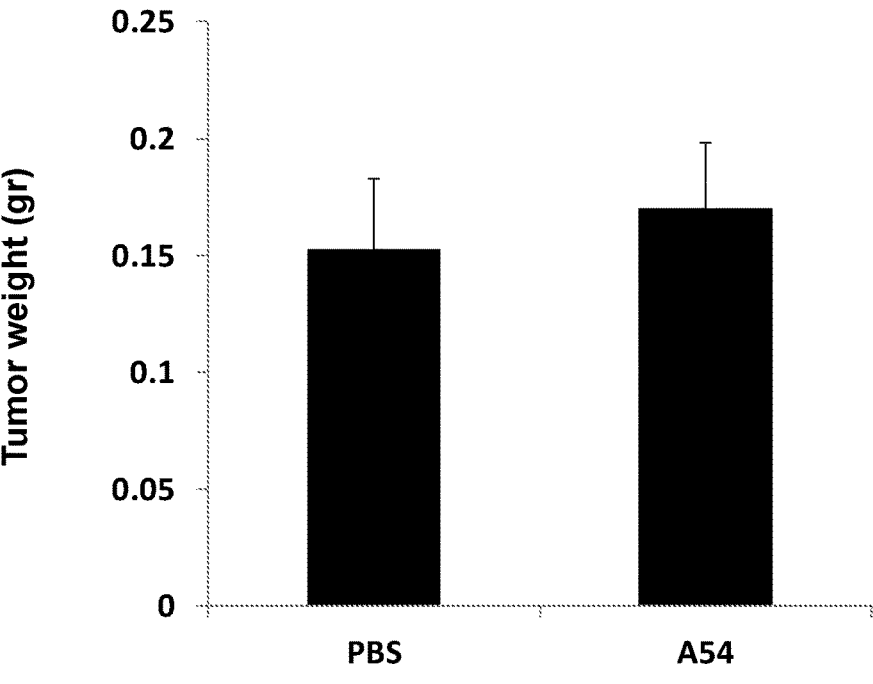
Figure 7D
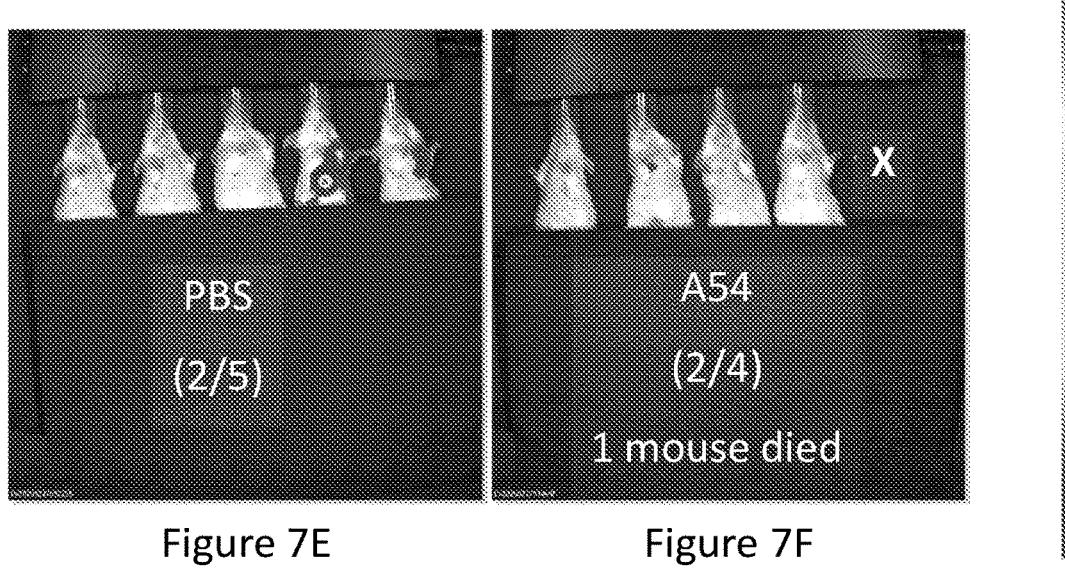
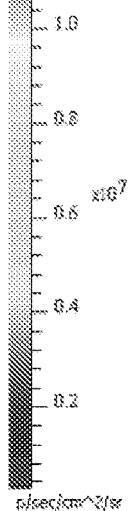
Figure 7E                    Figure 7F Figure 8A                    Figure 8B Figure 8C                    Figure 8D

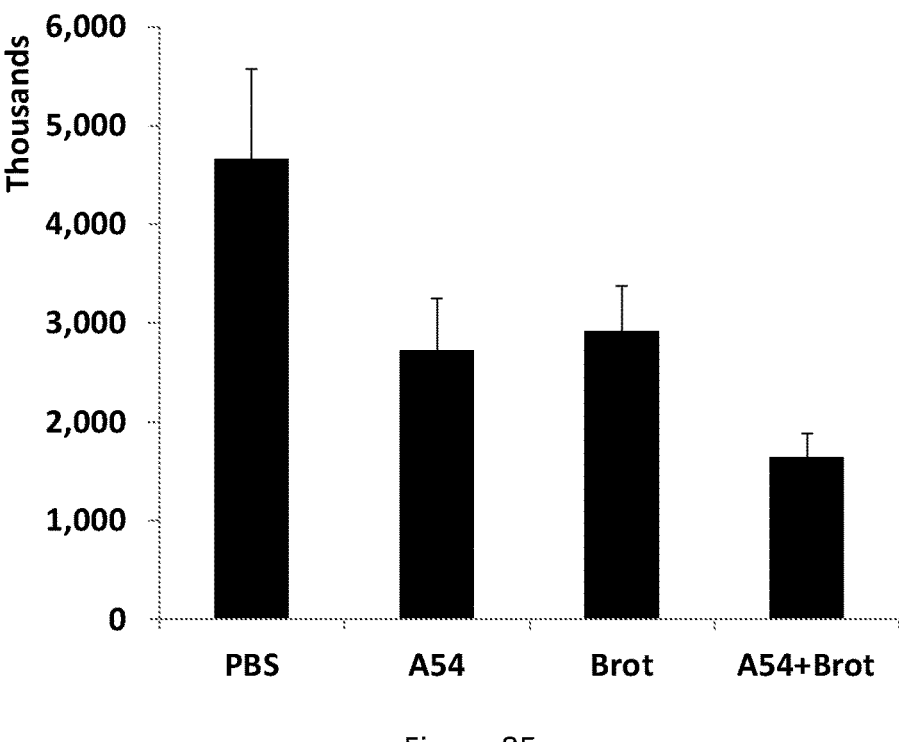
Figure 8E
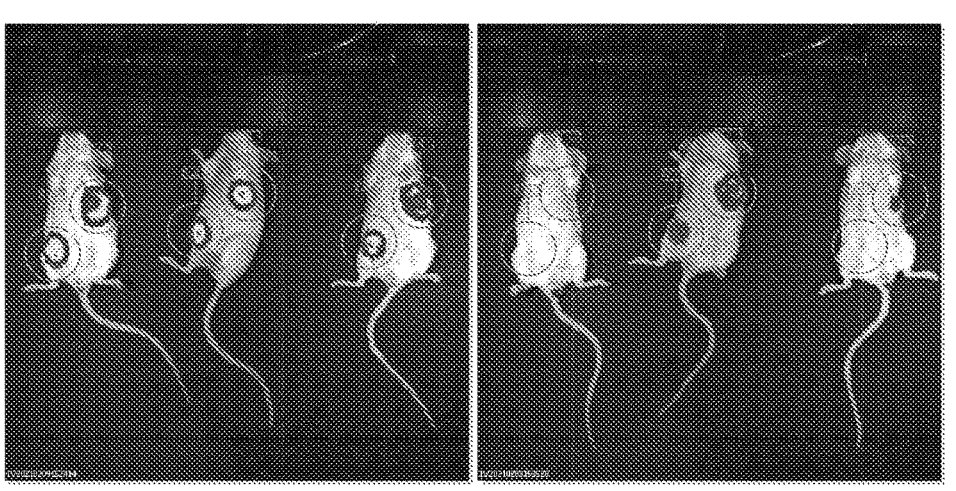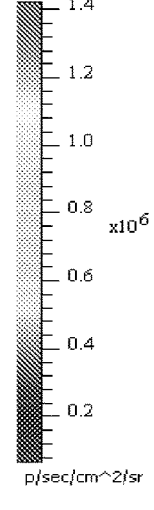
Figure 9A          Figure 9B

*Removes intact IgG and Fc fragments
**Captured IgG and Fc released

Figure 14A                  Figure 14B

HEPARANASE-NEUTRALIZING A54 MONOCLONAL ANTIBODY

CROSS-REFERENCE TO RELATED APPLICATIONS

This application is a National Phase Application of PCT International Application No. PCT/IL2021/050830, International Filing Date Jul. 6, 2021, which claims the benefit of U.S. Provisional Patent Application No. 63/048,211, filed Jul. 6, 2020, which are hereby incorporated by reference.

FIELD OF THE INVENTION

The present invention relates to heparanase-neutralizing monoclonal antibodies, pharmaceutical composition comprising same, and use thereof for treating a disease or disorder associated with heparanase activity in a subject.

BACKGROUND OF THE INVENTION

Heparanase is an endo-β-D-glucuronidase capable of cleaving heparan sulfate (HS) side chains at a limited number of sites. Heparanase activity correlates with the metastatic potential of tumor-derived cells, attributed to enhanced cell dissemination as a consequence of HS cleavage and remodeling of the extracellular matrix (ECM) and basement membrane underlying epithelial and endothelial cells. Heparanase expression is induced in all major types of human cancer namely carcinomas, sarcomas and hematological malignancies. Increased heparanase levels are most often associated with reduced patients' survival post operation, increased tumor metastasis and higher microvessel density. In addition, heparanase up-regulation was associated with tumor larger in size. Likewise, heparanase overexpression enhanced, while local delivery of anti-heparanase siRNA inhibited the growth of tumor xenografts. These results imply that heparanase function is not limited to tumor metastasis but is engaged in progression of the primary lesion, thus critically supporting the intimate involvement of heparanase in tumor progression and encouraging the development of heparanase inhibitors as anti-cancer therapeutics.

Heparanase has also been shown to facilitate cell invasion associated with autoimmunity, inflammation (Lerner et al. J Clin Invest 2011; 121 (5): 1709-21) and angiogenesis (Vlodavsky et al., Invasion & Metastasis 1992; 12, 112-127). In addition, increased heparanase expression has been noted in kidney (Levidiotis et al., Kidney Int. 60, 1287-1296, 2001; Abassi and Goligorsky M S. Adv Exp Med Biol. 2020; 1221:685-702; van der Vlag and Buijsers. Adv Exp Med Biol. 2020; 1221:647-667), liver (Xiao et al., Hepatology Res. 26, 192-198, 2003) and diabetic (Katz et al., Isr. Med. Assoc. 4, 996-1002, 2002; Gil et al. Diabetes 2012; 61:208-16, Simconovic et al., Adv Exp Med Biol. 2020; 1221:607-630, and Ziolkowski et al. 2012; 122:132-41) disorders. Heparanase is also involved in acute pancreatitis (Khamaysi et al., Adv Exp Med Biol. 2020; 1221:703-719), cardiomyopathy (Shang et al., Adv Exp Med Biol. 2020; 1221:721-745), amyloidosis (Li J P and Zhang X. Adv Exp Med Biol. 2020; 1221:631-645), viral infections (Agelidis A, Shukla D. Adv Exp Med Biol. 2020; 1221:759-770).

The finding that heparanase is involved in a wide variety of pathological processes has led to development of therapeutic compounds to inhibit this enzyme including, PI-88, a phosphomannopentaose sulfate (Chhabra and Ferro, Adv Exp Med Biol. 2020; 1221:473-491), PG545 (Hammond and Dredge, Adv Exp Med Biol. 2020; 1221:539-565) and Roneparstat, a modified heparin that is 100% N-acetylated and 25% glycol split. Roneparstat is endowed with little or no anti-coagulant activity, exerts highly diminished undesired release and activation of ECM-bound pro-angiogenic factors (i.e., bFGF) (Casu et al. Pathophysiolog Haemost Thromb 2008; 36(3-4):195-203; Naggi et al. J Biol Chem 2005; 280 (13): 12103-13), and has proven efficacious in several tumor model systems (Ritchie et al, 2011, ibid; Yang et al. Blood 2007; 110 (6): 2041-8. Noseda and Barbieri, Adv Exp Med Biol. 2020; 1221:523-538), yet it may still exhibit heparanase enzymatic activity-unrelated properties (Levidiotis et al. Nephrology (Carlton) 2005; 10(2): 167-73).

Three potential heparin-binding domains of heparanase were identified by the present inventors and co-workers (Levy-Adam et al. Id J Biol Chem 2005; 280 (21): 20457-66). Particular attention was given to the $Lys^{158}$-$Asp^{171}$ domain since a peptide corresponding to this sequence (termed KKDC) physically interacts with heparin and HS with high affinity and inhibits heparanase enzymatic activity. Furthermore, deletion construct lacking this domain exhibits no enzymatic activity and polyclonal antibody (Ab #733) directed to this region inhibits heparanase activity (Zetser et al. J Cell Sci 2004; 117(11): 2249-58).

Attempts to inhibit heparanase enzymatic activity were initiated already at the early days of heparanase research, in parallel with the emerging clinical relevance of this activity. More recently, a variety of inhibitory molecules have been developed, including peptides, small molecules (Giannini et al., Adv Exp Med Biol. 2020; 1221:567-603), modified non-anticoagulant species of heparin, as well as several other polyanionic molecules such as laminaran sulfate, suramin, PI-88, and PG545 (Dredge et al. Br J Cancer 2011, 635-42, Hammond and Dredge, Adv Exp Med Biol. 2020; 1221:539-565). Similarly, anti-heparanase polyclonal antibodies were developed and demonstrated to neutralize heparanase enzymatic activity and to inhibit cell invasion (He X et al. Cancer Res 2004; 64(11): 3928-33), proteinuria (Levidiotis V, et al. Nephrology (Carlton) 2005; 10(2): 167-73) and neointima formation (Myler H A, et al. J Biochem 2006; 139:339-45). Neutralizing anti-heparanase monoclonal antibodies, were recently reported (Weissmann et al., PNAS 113:704-709, 2016).

U.S. Pat. No. 7,772,187 by some of the inventors of the present invention relates to an amino acid sequence derived from the N' terminus region of the 50 Kd subunit of heparanase, and particularly to the sequence of $Lys^{158}$-$Asn^{171}$ of human heparanase. The '187 patent further discloses a polyclonal antibody directed to the sequence and compositions and uses thereof as heparanase inhibitor.

U.S. Pat. No. 6,562,950 by an inventor of the present invention and coworkers provides a monoclonal antibody elicited by a heparanase protein or an immunogenic portion thereof, which specifically inhibits heparanase activity. The '950 patent disclosed two monoclonal antibodies HP-130 and H-239. Notably, the HP-239 which recognized an internal epitope localized to amino acids 130-230 caused no inhibition of heparanase activity whereas HP-130 formed against the C-terminus of heparanase almost completely inhibited its activity.

U.S. Pat. No. 8,048,993 by an inventor of the present invention and coworkers provides an antibody that specifically binds an epitope of a heparanase protein provided that phenylalanine replaces tyrosine at position 246 of the heparanase protein.

PCT WO 2017/064716 A1 describes specific monoclonal antibody termed 9E8 which binds the $Lys^{158}$-$Asp^{171}$ domain of heparanase, neutralizes heparanase enzymatic activity and attenuates lymphoma and myeloma tumor progression (Weissmann et al., PNAS 113:704-709, 2016). IgG clones S9-C1 and C6-S4-C3 were derived from IgM 9E8.

Thus, there is an unmet need to provide highly specific heparanase-neutralizing monoclonal antibodies which can be used to prevent and treat medical conditions associated with heparanase activity.

SUMMARY OF THE INVENTION

The present invention provides heparanase-neutralizing IgG monoclonal antibody (mAb A54), pharmaceutical composition comprising same, and use thereof for treating a disease or disorder associated with heparanase activity, including but not limited to malignant proliferative diseases.

mAb A54 of the invention is useful in attenuating and treating diseases and disorders associated with heparanase enzymatic activity, as a single agent or in combination with at least one additional conventional therapy including but not limited to chemotherapy or radiation.

According to a first aspect, the present invention provides a neutralizing monoclonal antibody (mAb), or an antibody fragment comprising at least an antigen-binding portion thereof. According to another embodiment the mAb or antibody fragment thereof has a heparanase neutralizing effect.

According to another embodiment the antibody fragment is selected from the group consisting of: Fab, Fab', F(ab')₂, Fd, Fd', Fv, dAb, isolated CDR region, single chain antibody, diabodies, and linear antibodies According to another aspect the present invention provides an isolated polynucleotide sequence encoding the mAb of the invention or an antibody fragment thereof.

According to another aspect there is provided a vector comprising the polynucleotide sequence encoding the mAb or antibody fragment thereof of the invention. According to yet another aspect there is provided a host cell comprising the vector of the invention.

According to another aspect there is provided a pharmaceutical composition comprising the mAb of the invention, or an antibody fragment thereof, and a pharmaceutical acceptable carrier.

According to another aspect there is provided a method for treating a disease or disorder associated with heparanase activity in a subject in need thereof, comprising administering to the subject a therapeutically effective amount of the mAb of the invention or an antibody fragment thereof, thereby treating the heparanase-associated disease or disorder in said subject.

In some embodiments, the method comprises administering to the subject a pharmaceutical composition comprising the mAb of the invention, or an antibody fragment thereof, and a pharmaceutical acceptable carrier.

In some embodiments of the methods of the invention, the disease or disorder associated with heparanase activity is selected from the group consisting of: a malignant proliferative disease, an inflammatory disorder, an autoimmune disorder, viral infection, diabetes and related kidney dysfunction.

In some embodiments of the methods of the invention, the disease or disorder associated with heparanase activity is a malignant proliferative disease, such as cancer.

According to another embodiment, the proliferative disease is a solid malignancy including but not limited to carcinoma and sarcoma. According to particular embodiments, the solid malignancy is melanoma. According to particular embodiments, the solid malignancy is selected from the group consisting of: breast cancer, prostate cancer, skin cancer, colon cancer, lung cancer, pancreatic cancer, head and neck cancer, kidney cancer, ovarian cancer, cervix cancer, bone cancer, liver cancer, thyroid cancer, tongue cancer and brain cancer.

According to certain embodiments, the proliferative disease is a hematopoietic malignancy, such as lymphoma, leukemia and multiple myeloma. According to particular embodiments, the hematopoietic malignancy is selected from the group consisting of: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

In another embodiment, the methods of the invention reduce or inhibit tumor metastasis in said subject. In another embodiment, the methods of the invention inhibit tumor progression in said subject.

In some embodiments of the methods of the invention, the disease or disorder associated with heparanase activity is an inflammatory disorder, an autoimmune disorder, viral infection, and a kidney disorder.

In particular embodiments of the methods of the invention, the subject is a mammal. In some embodiment, the subject is a human. In some embodiments, the subject is male. In some embodiments, the subject is female. In some embodiments, the subject is an adult. In some embodiments, the subject is a child.

According to another aspect there is provided a method for treating a disease or disorder associated with heparanase activity, the method comprising administering to a subject in need thereof an effective amount of a mAb of the invention or a fragment thereof, in combination with at least one anti-cancer treatment; thereby treating the heparanase-associated disease or disorder. In some embodiments, the anti-cancer treatment is selected from chemotherapy and radiation therapy.

According to another aspect there is provided a method for neutralizing heparanase activity comprising contacting a cell with the mAb of the invention or an antibody fragment thereof.

Further embodiments and the full scope of applicability of the present invention will become apparent from the detailed description given hereinafter.

According to another aspect there is provided an antibody or an antigen-binding fragment, analog or derivative thereof, directed against a heparanase enzyme, wherein the antibody, antigen-binding fragment, analog or derivative thereof comprises at least one complementarity-determining region (CDR), wherein the CDR comprises SEQ ID NO: 1 to SEQ ID NO: 6, or a combination thereof.

According to another aspect there is provided an antibody or an antigen-binding fragment, analog or derivative thereof, directed against an HBD-II region (heparin-binding domain 2) of a heparanase enzyme, wherein the antibody, antigen-binding fragment, analog or derivative thereof comprises at least one complementarity-determining region (CDR), wherein the CDR comprises SEQ ID NO: 1 to SEQ ID NO: 6, or a combination thereof.

In some embodiments, the antibody or fragment is a murine or human antibody or fragment or is a humanized antibody or fragment.

According to another aspect there is provided a method for suppressing, inhibiting, preventing or treating a disease or disorder associated with heparanase activity in a subject in need thereof, comprising administering to the subject a therapeutically effective amount of an antibody or an anti-
gen-binding fragment, analog or derivative thereof, directed
against a heparanase enzyme, or directed against HBD-II
region (heparin-binding domain 2), wherein the antibody, or
antigen-binding fragment, analog or derivative thereof,
comprises at least one complementarity-determining region
(CDR), wherein the CDR comprises SEQ ID NO: 1 to SEQ
ID NO: 6, or a combination thereof.

According to another aspect there is provided a method
for inhibiting or treating a disease or disorder associated
with heparanase activity in a subject in need thereof, com-
prising administering to the subject a therapeutically effec-
tive amount of an antibody or an antigen-binding fragment,
analog or derivative thereof, directed against a heparanase
enzyme, wherein the antibody, or antigen-binding fragment,
analog or derivative thereof, comprises at least one comple-
mentarity-determining region (CDR), wherein the CDR
comprises SEQ ID NO: 1 to SEQ ID NO: 6, or a combina-
tion thereof.

According to another aspect there is provided a method
for inhibiting or treating a disease or disorder associated
with heparanase activity in a subject in need thereof, com-
prising administering to the subject a therapeutically effec-
tive amount of an antibody or an antigen-binding fragment,
analog or derivative thereof, directed against an HBD-II
region (heparin-binding domain 2) of a heparanase enzyme,
wherein the antibody, or antigen-binding fragment, analog
or derivative thereof, comprises at least one complementar-
ity-determining region (CDR), wherein the CDR comprises
SEQ ID NO: 1 to SEQ ID NO: 6, or a combination thereof.

BRIEF DESCRIPTION OF THE DRAWINGS

FIGS. 3A and 3B are line graphs representing an activity
assay of purified recombinant active heparanase pre-incu-
bated with 0.1 µg/ml (FIG. 3B) or 1 µg/ml (FIG. 3A) purified
mAb A54 vs. control mouse IgG FIGS. 4A-C depict the invasion of U87 human glioma
cells in the presence of mouse IgG or mAb A54. FIGS. 4A-B
show photomicrographs and FIG. 4C is a bar graph repre-
senting the extent of cell invasion through a reconstituted
basement membrane.

FIGS. 5A, 5B, 5D and 5E are photographs representing
the luciferase in vivo imaging (IVIS) of human myeloma
(FIGS. 5A and 5B) and glioma (FIGS. 5D and 5E) tumors
growing in NOS/SCID mice, in the absence (PBS) and
presence of mAb A54. FIGS. 5C and 5F are bar graphs
representing quantification of the respective luciferase sig-
nals.

FIGS. 6A-C represent the effect of mAb A54 in attenu-
ating MPC-11 mouse myeloma tumor growth compared to
tumor bearing mice treated with PBS (control).

FIGS. 7A and 7B are photographs representing the
luciferase florescence in vivo imaging (IVIS) of mouse 4T1
breast carcinoma tumors growing in the mammary fad pad
of Balb/c mice, in the absence (PBS) and presence of mAb
A54.
FIG. 7D is a bar graph
representing the weights of 4T1 primary tumors excised from Balb/c mice treated with vehicle (PBS) or with mAb
A54 as described in FIGS. 7A and 7B.

FIGS. 7E and 7F are photographs representing the lucifer-
ase florescence in vivo imaging (IVIS) of 4T1 metastatic
lesions detected in Balb/c mice, after removal of the primary
tumors, treated with vehicle (PBS) or mAb A54.

FIGS. 8A-D are photographs representing the luciferase
florescence in vivo imaging (IVIS) of human myeloma
tumors growing in NOS/SCID mice, in the absence (PBS)
and presence of mAb A54 (FIGS. 8A and 8B respectively)
and in the presence of Brotezomib and the presence of mAb
A54+Brotezomib (FIGS. 8C and 8D respectively). FIG. 8E
is a bar graph representing quantification of the respective
luciferase signals.

FIGS. 9A and 9B are photographs representing the
luciferase florescence in vivo imaging (IVIS) of mouse
breast carcinoma tumors growing in the mammary fad pad
of Balb/c mice, in the absence (PBS) and presence of mAb
A54.

FIGS. 14A and 14B are schematic illustration showing
A54 binding interaction with HPSE (β/α) 8-barrel from two
different angles.

DETAILED DESCRIPTION OF THE INVENTION

The present invention relates to heparanase-neutralizing
monoclonal antibodies (mAbs), pharmaceutical composition
comprising same, and use thereof for treating a disease or disorder associated with heparanase activity, including but not limited to malignant diseases.

Figure 1:
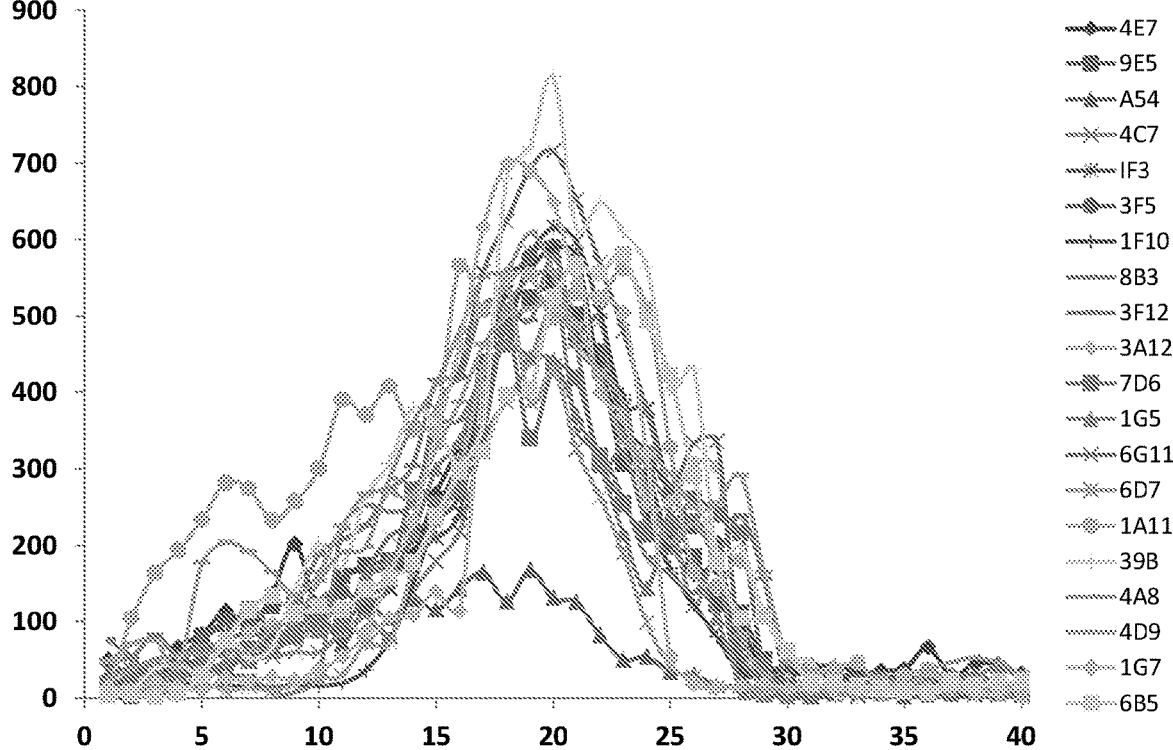
FIG. 1 is a line graph representing an activity assay of
heparanase with various hybridomas.
Figure 2A:
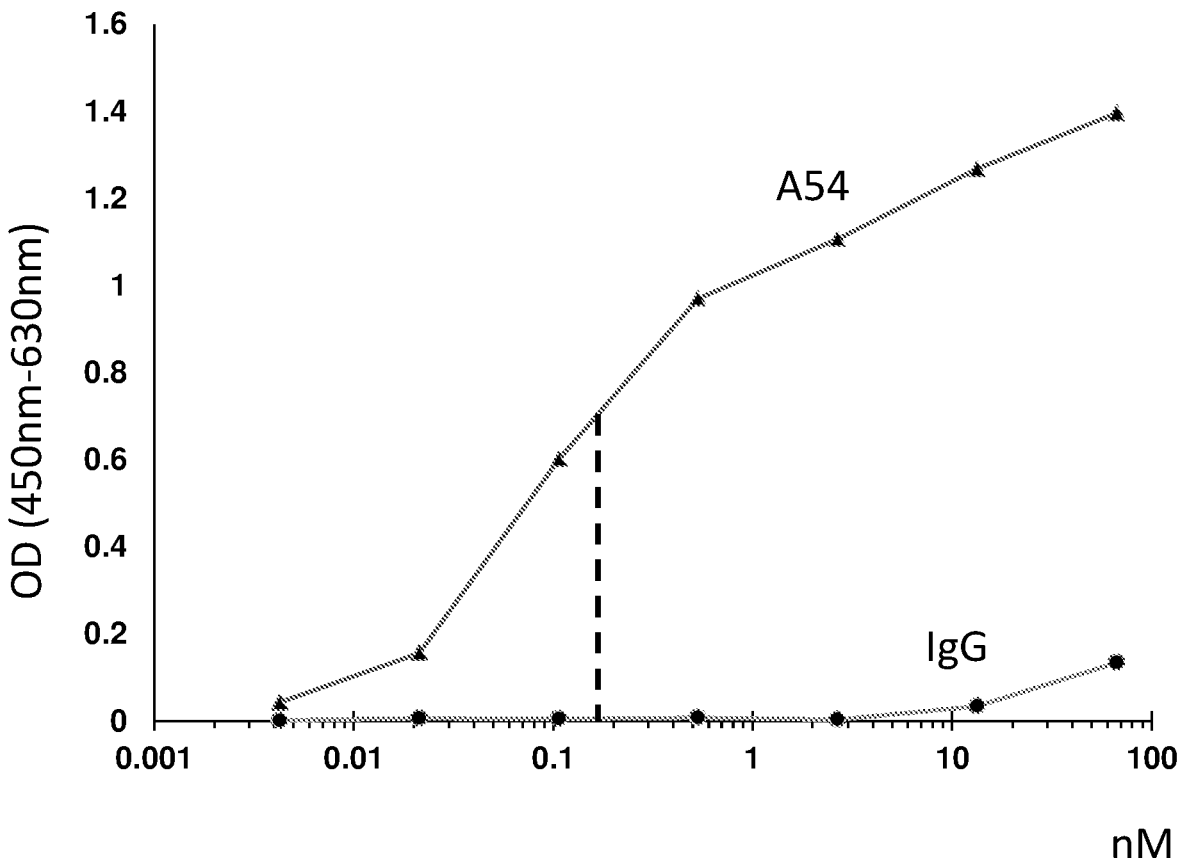
FIG. 2A is a line graph representing the binding of
increasing concentrations of mAb 54 vs. control mouse IgG
to immobilized latent heparanase.
Figures 2B, 2C:
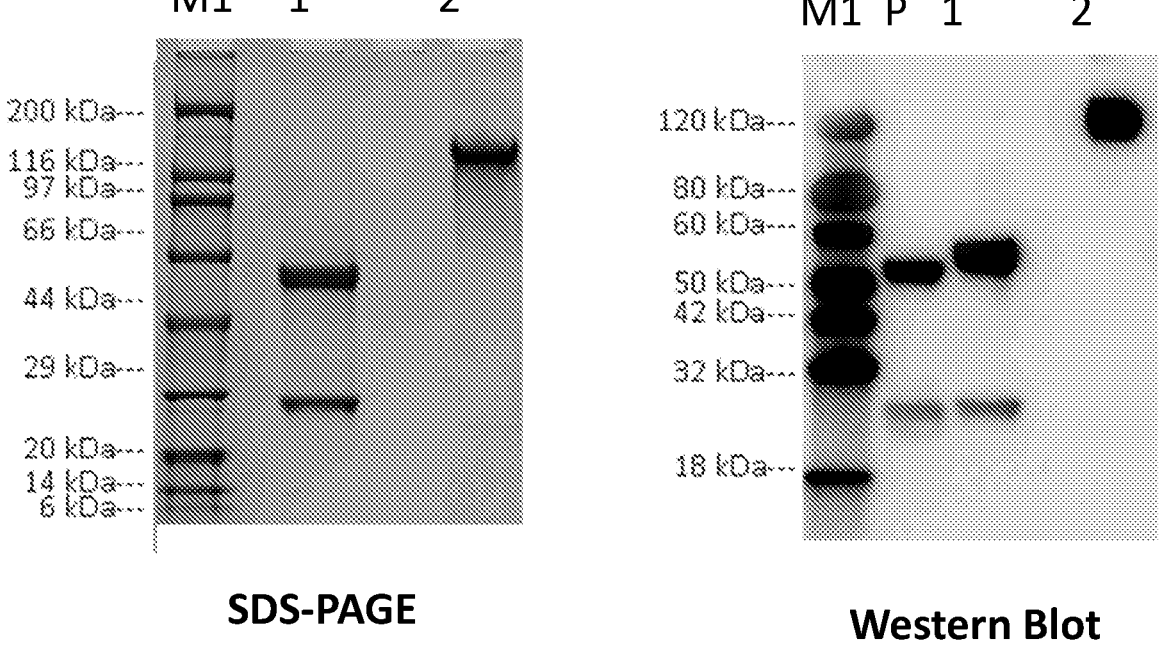
FIG. 2B is an SDS-PAGE and FIG. 2C is a Western blot
analyses of A54 mAb heavy chains (HC) and light chains
(LC).
Figure 3A:
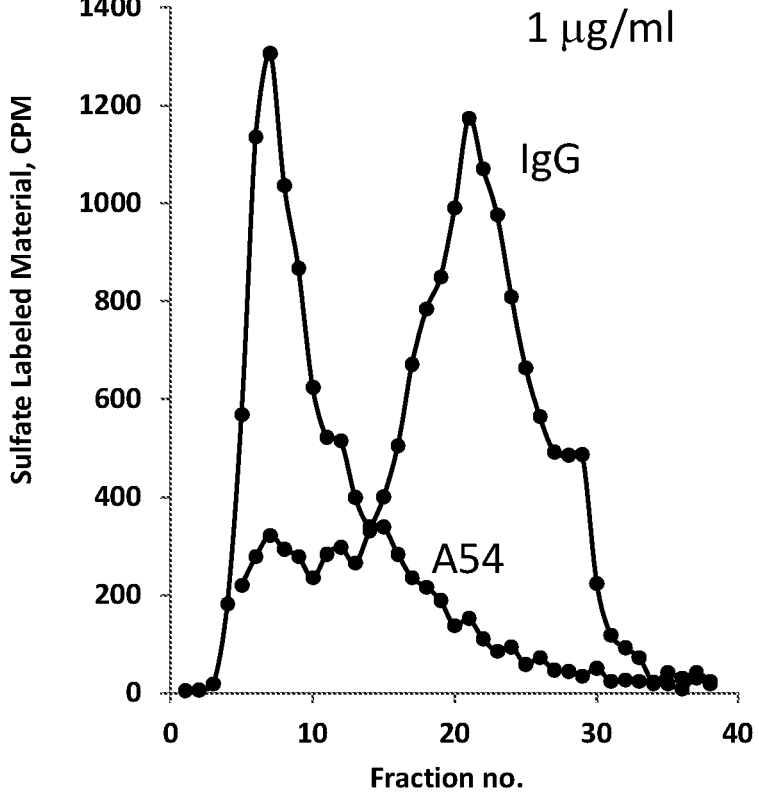
Figure 5F:
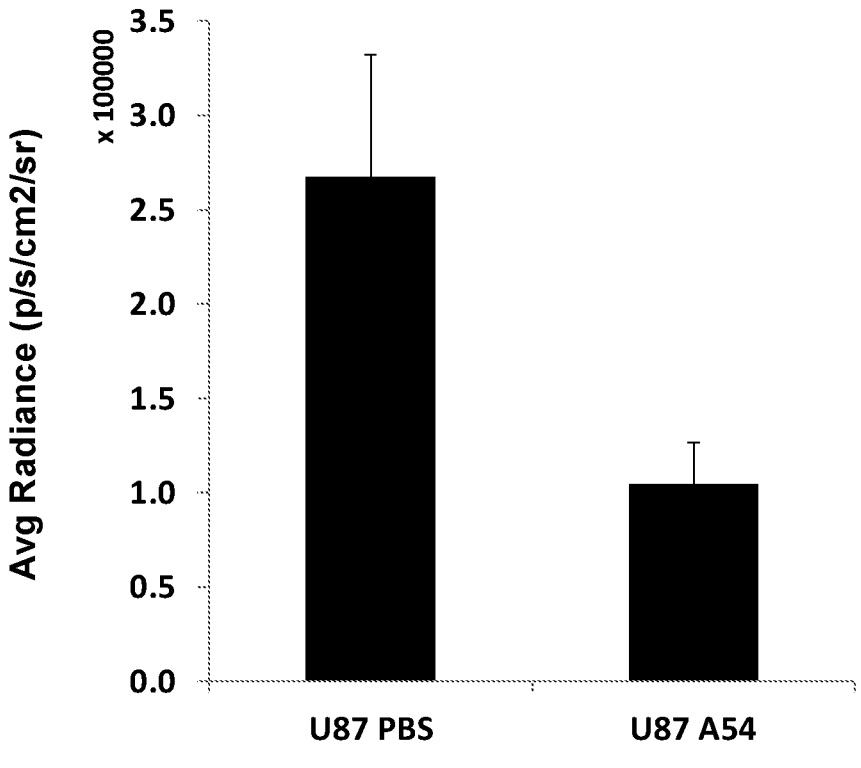
Figure 14C:
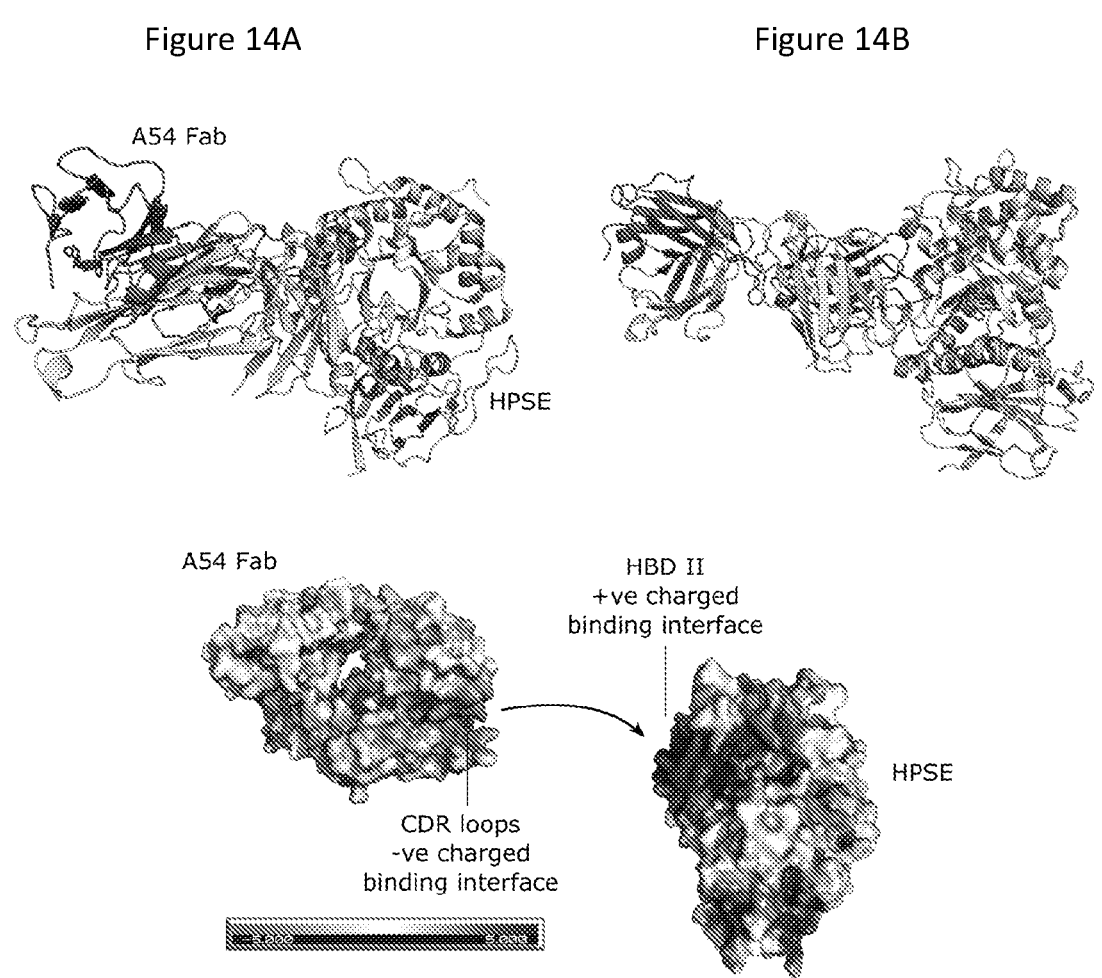
FIG. 14C is an electrostatic surface repre-
sentation showing the strong contribution of electrostatic
charge to A54-HPSE binding.

The present invention is based, in part, on the development of a mAb which binds the heparanase protein (HPSE) (FIGS. 2A-2C) and neutralizes heparanase enzymatic activity (FIGS. 1 and 3A-3B). As demonstrated herein, the mAb markedly inhibited cellular invasion through Matrigel, a reconstituted basement membrane (FIGS. 4A-4C). Treatment with the mAb, as a single agent, resulted in smaller human myeloma (CAG) and glioma (U87) tumor xenografts (FIGS. 5A, 5B, 5D and 5E) growing in NOD/SCID mice as revealed by an in vivo imaging system (IVIS) of luciferase fluorescence (FIGS. 5C and 5F). Likewise, mAb A54 attenuated mouse myeloma (MPC-11) tumor growth in a syngeneic Balb/c mouse model (FIGS. 6A-6C). mAb A54 also inhibited spontaneous metastasis of 4T1 mouse breast carcinoma in an orthotopic syngeneic Balb/c mouse model (FIGS. 7A-7D). Further, the heparanase protein has multiple binding locations, including, but not limited to, HBD-I (heparin-binding domain 1) and HBD-II (heparin-binding domain 2). The majority of mAb A54 interactions are with HBD-II (as detailed in Example 12). The mAb A54 CDR loops mediate nearly all the A54-HPSE binding interactions. A54 Fab binds to HPSE on the (B/a) 8-barrel domain, right above HBD-II (Gln270-Lys280; FIGS. 14A and 14B). This interaction prevents HPSE from binding its HS substrates by steric occlusion of the enzyme binding cleft. Protein surface charges shows a major electrostatic contribution to the A54-HPSE interaction. HBD-II is substantially positively charged, whereas the binding interface of A54 is negatively charged (FIG. 14C).

mAb A54 exerts high specificity, enabling solely the targeting of heparanase enzymatic activity. Thus, the antibodies of the invention are useful in attenuating and treating diseases and disorders associated with heparanase activity, including but not limited to, tumor progression, inflammation, type 1 diabetes, diabetic nephropathy, and viral infection as single agent or in combination with at least one additional therapy including but not limited to chemotherapy or radiation.

According to another embodiment a mAb or antibody fragment thereof is provided comprising at least one heavy-chain CDR selected from the group consisting of: a heavy-chain CDR1 (CDR-H1) comprising a sequence set forth in SEQ ID NO: 1 (GYTFTN); a heavy-chain CDR2 (CDR-H2) comprising a sequence set forth in SEQ ID NO: 2 (YINPTTGYTEYNQKFKD); and a heavy-chain CDR3 (CDR-H3) comprising a sequence set forth in SEQ ID NO: 3 (GGAGYDYDEDYAMDY).

According to another embodiment a mAb or antibody fragment thereof is provided comprising a heavy-chain CDR1 (CDR-H1) comprising a sequence set forth in SEQ ID NO: 1 (GYTFTN) (short sequence); a heavy-chain CDR2 (CDR-H2) comprising a sequence set forth in SEQ ID NO: 2 (YINPTTGYTEYNQKFKD); and a heavy-chain CDR3 (CDR-H3) comprising a sequence set forth in SEQ ID NO: 3 (GGAGYDYDEDYAMDY).

According to another embodiment a mAb or antibody fragment thereof is provided comprising at least one light-chain CDR selected from the group consisting of: a light-chain CDR1 (CDR-L1) comprising a sequence set forth in SEQ ID NO: 4 (RASESVEYFGTSYMN); a light-chain CDR2 (CDR-L2) comprising a sequence set forth in SEQ ID NO: 5 (LASILES); and a light-chain CDR3 (CDR-L3) comprising a sequence set forth in SEQ ID NO: 6 (QQSNEDPYT).

According to another embodiment a mAb or antibody fragment thereof is provided comprising a light-chain CDR1 (CDR-L1) comprising a sequence set forth in SEQ ID NO: 4 (RASESVEYFGTSYMN); a light-chain CDR2 (CDR-L2) comprising a sequence set forth in SEQ ID NO: 5 (LASILES); and a light-chain CDR3 (CDR-L3) comprising a sequence set forth in SEQ ID NO: 6 (QQSNEDPYT).

According to another embodiment a mAb or antibody fragment thereof is provided comprising at least one heavy-chain CDR selected from the group consisting of: a heavy-chain CDR1 (CDR-H1) comprising a sequence set forth in SEQ ID NO: 1 (GYTFTN); a heavy-chain CDR2 (CDR-H2) comprising a sequence set forth in SEQ ID NO: 2 (YINPTTGYTEYNQKFKD); and a heavy-chain CDR3 (CDR-H3) comprising a sequence set forth in SEQ ID NO: 3 (GGAGYDYDEDYAMDY), and comprising at least one light-chain CDR selected from the group consisting of: a light-chain CDR1 (CDR-L1) comprising a sequence set forth in SEQ ID NO: 4 (RASESVEYFGTSYMN); a light-chain CDR2 (CDR-L2) comprising a sequence set forth in SEQ ID NO: 5 (LASILES); and a light-chain CDR3 (CDR-L3) comprising a sequence set forth in SEQ ID NO: 6 (QQSNEDPYT).

According to another embodiment a mAb or antibody fragment thereof is provided comprising a heavy-chain CDR1 (CDR-H1) comprising a sequence set forth in SEQ ID NO: 1 (GYTFTN); a heavy-chain CDR2 (CDR-H2) comprising a sequence set forth in SEQ ID NO: 2 (YINPTTGYTEYNQKFKD); and a heavy-chain CDR3 (CDR-H3) comprising a sequence set forth in SEQ ID NO: 3 (GGAGYDYDEDYAMDY), and comprising a light-chain CDR1 (CDR-L1) comprising a sequence set forth in SEQ ID NO: 4 (RASESVEYFGTSYMN); a light-chain CDR2 (CDR-L2) comprising a sequence set forth in SEQ ID NO: 5 (LASILES); and a light-chain CDR3 (CDR-L3) comprising a sequence set forth in SEQ ID NO: 6 (QQSNEDPYT).

According to another embodiment, the heavy-chain CDR1 (CDR-H1) comprising the short sequence set forth in SEQ ID NO: 1 (GYTFTN) may be replaced by a heavy-chain CDR1 (CDR-H1) comprising a long sequence set forth in SEQ ID NO: 17 (GYTFTNYWMH).

According to some embodiments, the present invention provides a mAb or antibody fragment thereof comprising a heavy chain variable domain sequence having an amino acid sequence set forth in SEQ ID NO: 7: QVQLQQSGAEL-AKPGASVRMSCKASGYTFTNYWMHWVKQRPGQ-GLEWIGYI NPTTGYTEYNQKFKDKATLTADKSSS-TAYMQLSSLTSEDSAVYYCARGGAGY DYDEDYA-MDYWGQGTSVTVSS or an analog or derivative thereof having at least 70% sequence identity with the heavy chain sequence. In some embodiments, the analog or derivative has at least 75%, at least 80%, at least 85%, at least 90% or at least 95% sequence identity with SEQ ID NO: 7.

According to another embodiment, the present invention provides a mAb or antibody fragment thereof comprising a light chain variable domain sequence having an amino acid sequence set forth in SEQ ID NO: 8: DIVLTQSPASLAVSLGQRATISCRASESVEYFGTSYM-NWYQQKPGQPPKLLIYL ASILESGIPARFSGSGSG-TDFTLNIHPVEEEDAATYYCQQSNEDPYTFGGGTK-LEIK, or an analog or derivative thereof having at least 70% sequence identity with the light chain sequence. In some embodiments, the analog or derivative has at least 75%, at least 80%, at least 85%, at least 90% or at least 95% sequence identity with SEQ ID NO: 8.

According to a specific embodiment the antibody or fragment thereof comprises a heavy chain variable domain having a sequence set forth in SEQ ID NO: 7 and a light chain variable domain having a sequence set forth in SEQ ID NO: 8.

Analogs and derivatives of the monoclonal antibody or fragment thereof, having at least 70% sequence identity with the antigen-binding portion of the reference sequence are also within the scope of the present invention. According to some embodiments, analogs and derivatives of the monoclonal antibody or fragment thereof having at least 80%, at least 85%, at least 90% or at least 95% sequence identity with the antigen-binding portion of the reference sequence are provided.

The term "having at least X percent identity" refers to the percent of amino acid residues that are identical in the two compared sequences when the sequences are optimally aligned. Thus, 70% amino acid sequence identity means that 70% of the amino acids in two or more optimally aligned polypeptide sequences are identical.

A monoclonal antibody according to the present invention may contain a constant region from any mammalian species, including but not limited to mouse, rat and human. A monoclonal antibody according to the present invention includes a chimeric antibody, a humanized antibody, a fully human antibody, a xenogeneic antibody, and an antibody fragment comprising at least the antigen-binding portion of an antibody.

The present invention encompasses monoclonal antibodies isolated from hybridoma cells or other biological systems, as well as monoclonal antibodies produced recombinantly or synthetically. The hybridomas may be prepared by any of the methods known in the art (for example, Kohler, G. and Milstein, C., *Nature,* 256:495-497, (1975)). The supernatant of the hybridoma cell lines are typically screened for antibody binding activity by any one of the methods known in the art such as by enzyme linked immuno sorbent assay (ELISA) or radio immuno assay (RIA). The supernatants may be screened for production of mAbs which inhibit heparanase enzymatic activity.

DNA sequences which encode any of the amino acid sequences of the heavy chain or light chain of the above mAbs are also encompassed within the scope of the invention. As will no doubt be clear to any person skilled in the art, due to the degenerative nature of the genetic code a plurality of nucleic acid sequences may code for the mAb of the invention beyond those shown in SEQ ID NO: 9 or SEQ ID NO: 10. The invention also provides expression vectors such as plasmids having said DNA sequences as well as host cells containing one or more of these expression vectors.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (fragment crystalline) domains. The antigen binding domains, Fab, include regions where the polypeptide sequence varies. The term $F(ab')_2$ represents two Fab' arms linked together by disulfide bonds. The central axis of the antibody is termed the Fc fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains on the light and heavy chains have the same general structure and each domain comprises four framework regions, whose sequences are relatively conserved, joined by three hypervariable domains known as complementarity determining regions (CDR1-3). These domains contribute specificity and affinity of the antigen-binding site. The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments so long as they exhibit the desired biological activity.

The antibody according to the present invention is a molecule comprising at least the antigen-binding portion of an antibody. In specific embodiments, the antibody or antibodies according to the invention are monoclonal antibodies (mAbs), as well as proteolytic fragments thereof such as the Fab or $F(ab')_2$ fragments. Further included within the scope of the invention are chimeric antibodies; human and humanized antibodies; recombinant and engineered antibodies, and fragments thereof. Furthermore, the DNA encoding the variable region of the antibody can be inserted into the DNA encoding other antibodies to produce chimeric antibodies. Single chain antibodies also fall within the scope of the present invention.

"Antibody fragments" comprise a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) F(ab') 2 fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., PNAS (USA) 1988, 85, 5879-5883); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 1993, 90, 6444-6448); (xi) "linear antibodies" comprising a pair of tandem Fd segments (VH-CH1-VH-CH1) which, together with complementary light chain polypeptides, form a pair of antigen binding regions (Zapata et al. Protein Eng., 1995, 8, 1057-1062; and U.S. Pat. No. 5,641,870).

Single chain antibodies can be single chain composite polypeptides having antigen binding capabilities and comprising amino acid sequences homologous or analogous to the variable regions of an immunoglobulin light and heavy chain i.e. linked $V_H$-$V_L$ or single chain Fv (scFv).

A "neutralizing antibody" as used herein refers to a molecule having an antigen-binding site to a specific ligand target (e.g. heparanase or HBD-II) capable of reducing or inhibiting (blocking) activity or signaling through the target, as determined by in vivo or in vitro assays, as per the specification.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies to be used in accordance with the present invention may be made by the hybridoma method first described by Kohler et al., Nature 1975, 256, 495, or may be made by recombinant DNA methods (see, e.g., U.S. Pat. No. 4,816,567). The "monoclonal antibodies" may also be isolated from phage antibody libraries using the techniques described in Clackson et al., Nature 1991, 352, 624-628 or Marks et al., J. Mol. Biol., 1991, 222:581-597, for example.

The mAbs of the present invention may be of any immunoglobulin class including IgG, IgM, IgE, IgA, and any subclass thereof. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). In addition, complementarity determining region (CDR) grafting may be performed to alter certain properties of the antibody molecule including affinity or specificity. A non-limiting example of CDR grafting is disclosed in U.S. Pat. No. 5,225,539.

Chimeric antibodies are molecules, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (for example PCT patent applications WO 86/01533, WO 97/02671, WO 90/07861, WO 92/22653 and U.S. Pat. Nos. 5,693,762, 5,693,761, 5,585,089, 5,530,101 and 5,225,539).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 1986, 321, 522-525; Riechmann et al., Nature 1988, 332, 323-329; and Presta, Curr. Op. Struct. Biol., 1992 2, 593-596.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. Nature Biotechnology 1996 14, 309-314; Sheets et al. PNAS (USA), 1998, 95, 6157-6162); Hoogenboom and Winter, J. Mol. Biol., 1991, 227, 381; Marks et al., J. Mol. Biol., 1991, 222, 581). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al, Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg and Huszar, Intern. Rev. Immunol. 13:65-93 (1995). Alternatively, the human antibody may be prepared via immortalization of human B lymphocytes producing an antibody directed against a target antigen (such B lymphocytes may be recovered from an individual or may have been immunized in vitro). Sec, e.g., Cole et al., Monoclonal Antibodies and Cancer Therapy. Alan R. Liss. p. 77 (1985); Boerner et al., J. Immunol., 147 (1): 86-95 (1991); and U.S. Pat. No. 5,750,373.

By the term "single chain variable fragment (scFv)" is meant a fusion of the variable regions of the heavy and light chains of immunoglobulin, linked together with a short (usually serine, glycine) linker. Single chain antibodies can be single chain composite polypeptides having antigen binding capabilities and comprising amino acid sequences homologous or analogous to the variable regions of an immunoglobulin light and heavy chain (linked $V_H$-$V_L$ or single chain Fv (scFv)). Both $V_H$ and $V_L$ may copy natural monoclonal antibody sequences or one or both of the chains may comprise a CDR-FR construct of the type described in U.S. Pat. No. 5,091,513, the entire contents of which are incorporated herein by reference. The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are incorporated herein by reference.

A "molecule having the antigen-binding portion of an antibody" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see WO 93/15210, U.S. patent application Ser. No. 08/256,790, WO 96/13583, U.S. patent application Ser. No. 08/817,788, WO 96/37621, U.S. patent application Ser. No. 08/999,554, the entire contents of which are incorporated herein by reference), dimeric bispe- cific mini-antibodies (see Muller et al., 1998) and chimeric or single-chain antibodies incorporating such reactive frac- tion, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzy- matic cleavage, peptide synthesis or recombinant tech- niques.

For preparation of monoclonal antibodies, any technique known in the art that provides antibodies produced by continuous cell line cultures can be used. Examples include various techniques, such as those in Kohler, G. and Milstein, C., Nature 256:495-497 (1975); Kozbor et al., Immunology Today 4:72 (1983); Cole et al., pg. 77-96 in 'Monoclonal antibodies and cancer therapy', Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conven- tional method, many antigens prove to be non-immunogenic or extremely toxic, and therefore cannot be used to generate antibodies in animals. Moreover, affinity maturation (i.e., increasing the affinity and specificity) of recombinant anti- bodies is very simple and relatively fast. Finally, large numbers of different antibodies against a specific antigen can be generated in one selection procedure. To generate recombinant monoclonal antibodies one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recom- binant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Pro- tocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any meth- ods known in the art. In one method, the non-human complementarity determining regions (CDRs) are inserted into a human antibody or consensus antibody framework sequence. Further changes can then be introduced into the antibody framework to modulate affinity or immunogenicity.

Compositions, Administration and Dosages

For use in the methods of the invention, the monoclonal antibody may be formulated in a conventional manner using one or more pharmaceutically acceptable carriers, stabilizers or excipients (vehicles) to form a pharmaceutical composi- tion as is known in the art, in particular with respect to protein active agents. Carrier(s) are "acceptable" in the sense of being compatible with the other ingredients of the com- position and not deleterious to the recipient thereof. Suitable carriers typically include physiological saline or ethanol polyols such as glycerol or propylene glycol.

The antibody may be formulated as neutral or salt forms. Pharmaceutically acceptable salts include the acid addition salts (formed with free amino groups) and which are formed with inorganic acids such as hydrochloric or phosphoric acids, or such organic acids such as acetic, oxalic, tartaric and maleic. Salts formed with the free carboxyl groups may also be derived from inorganic bases such as sodium, potassium, ammonium, calcium, or ferric hydroxides, and organic bases as isopropylamine, trimethylamine, 2-ethyl- amino ethanol, histidine and procaine.

The compositions may be suitably formulated for intra- venous intramuscular, subcutaneous, or intraperitoneal administration and conveniently comprise sterile aqueous solutions of the antibody, which are preferably isotonic with the blood of the recipient. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example trehalose), amino acids, inorganic acids and admix- tures thereof. Stabilizers are used in aqueous solutions at the appropriate concentration and pH. The pH of the aqueous solution is adjusted to be within the range of 5.0-9.0, preferably within the range of 6-8. In formulating the antibody, anti-adsorption agent may be used. Other suitable excipients may typically include an antioxidant such as ascorbic acid.

The compositions may be formulated as controlled release preparations which may be achieved through the use of polymer to complex or absorb the proteins. Appropriate polymers for controlled release formulations include for example polyester, polyamino acids, polyvinyl, pyrrolidone, ethylenevinylacetate, and methylcellulose. Another possible method for controlled release is to incorporate the antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with carriers, such as lactose, sucrose, starch, talc magnesium stearate, crystalline cellulose, methyl cellulose, carboxymethyl cellulose, glycerin, sodium alginate or gum arabic.

The mAb of the invention may be administered parenterally, generally by intravenous infusion. Administration may also be by intraperitoneal, oral, subcutaneous, or intramuscular routes. Antibodies are generally administered in the range of about 0.1 to about 20 mg/kg of patient weight, commonly about 0.5 to about 10 mg/kg, and often about 1 to about 5 mg/kg. In this regard, it is preferred to use antibodies having a circulating half-life of at least 12 hours, preferably at least 4 days, more preferably up to 21 days. Chimeric and humanized antibodies are expected to have circulatory half-lives of up to four and up to 14-21 days, respectively. In some cases it may be advantageous to administer a large loading dose followed by periodic (e.g., weekly) maintenance doses over the treatment period. Antibodies can also be delivered by slow-release delivery systems, pumps, and other known delivery systems for continuous infusion. Dosing regimens may be varied to provide the desired circulating levels of a particular antibody based on its pharmacokinetics. Thus, doses will be calculated so that the desired circulating level of therapeutic agent is maintained.

Typically, the effective dose will be determined by the condition of the subject, as well as the body weight or surface area of the subject to be treated. The size of the dose and the dosing regimen also will be determined by the existence, nature, and extent of any adverse side effects that accompany the administration of the mAb or a combination of an additional therapeutic agent in a particular subject. In determining the effective amount of the therapeutic composition to be administered, the physician needs to evaluate inter alia circulating plasma levels, toxicity, and progression of the disease.

Chemotherapy

According to yet another embodiment there is provided combined cancer therapy comprising the administration of the mAb of the invention and at least one chemotherapeutic agent.

Chemotherapy drugs are divided into several groups based on their effect on cancer cells, the cellular activities or processes the drug interferes with, or the specific phases of the cell cycle the drug affects. Accordingly, chemotherapy drugs fall in one of the following categories: alkylating agents, nitrosoureas, antimetabolites, anthracyclines, topoi-somerase I and II inhibitors, mitotic inhibitors, inter alia platinum based drugs, steroids and anti-angiogenic agents.

Antimetabolites, also termed "nucleoside analogs", replace natural substances as building blocks in DNA molecules, thereby altering the function of enzymes required for cell metabolism and protein synthesis. In the event that they mimic nutrients required for cell growth, the cells eventually undergo lysis. If a nucleoside is replaced with a non-functional nucleoside analog, the latter is incorporated into DNA and RNA, finally inducing cell cycle arrest and apoptosis by inhibiting the cell's ability to synthesize DNA. Antimetabolites are cell-cycle specific and are most effective during the S-phase of cell division as they primarily act upon cells undergoing synthesis of new DNA for formation of new cells. The toxicities associated with these drugs are seen in cells that are growing and dividing quickly. Examples of antimetabolites include purine antagonists, pyrimidine antagonists, and folate antagonists. These agents damage cells during the S phase and are commonly used to treat leukemias, tumors of the breast, ovary, and the gastrointestinal tract, as well as other cancers. Specific examples of antimetabolites include 5-fluorouracil (also known as 5FU), capecitabine, 6-mercaptopurine, methotrexate, gemcitabine, cytarabine, fludarabine and pemetrexed.

Platinum-based chemotherapeutic drugs crosslink DNA in several different ways, interfering with cell division by mitosis. The damaged DNA elicits DNA repair mechanisms, which in turn activate apoptosis when repair proves impossible. Most notable among the DNA changes are the 1,2-intrastrand cross-links with purine bases. These include 1,2-intrastrand d(GpG) adducts which form nearly 90% of the adducts and the less common 1,2-intrastrand d(ApG) adducts. 1,3-intrastrand d(GpXpG) adducts occur but are readily excised by the nucleotide excision repair (NER). Other adducts include inter-strand crosslinks and nonfunctional adducts that have been postulated to contribute to the activity of platinum-based drugs. Interaction with cellular proteins, particularly HMG domain proteins, has also been advanced as a mechanism of interfering with mitosis, although this is probably not its primary method of action. Platinum-based chemotherapeutic drugs include cisplatin (also known as cisplatinum or cis-diamminedichloridoplatinum II (CDDP), carboplatin and oxaliplatin. Cisplatin is frequently designated as an alkylating agent, though it has no alkyl group and cannot carry out alkylating reactions. It is correctly classified as alkylating-like. Platinum-based chemotherapeutic drugs are used to treat various types of cancers, including sarcomas, some carcinomas (e.g. small cell lung cancer, and ovarian cancer), lymphomas and germ cell tumors.

Mitotic inhibitors interfere with cell division. The most known chemotherapeutic agent in this category is paclitaxel (also known as Taxol®, "plant alkaloid", "taxane" and an "antimicrotubule agent"). Together with docetaxel, it forms the drug category of the taxanes. However, other mitotic inhibitors are known, including, but not limited to etoposide, vinblastine and vincristine. Paclitaxel acts by interfering with normal microtubule growth during cell division by arrests their function; it hyper-stabilizes their structure. This destroys the cell's ability to use its cytoskeleton in a flexible manner. Specifically, paclitaxel binds to the B subunit of tubulin, the "building block" of microtubules, and the binding of paclitaxel locks these building blocks in place. The resulting microtubule/paclitaxel complex does not have the ability to disassemble. This adversely affects cell function because the shortening and lengthening of microtubules (termed dynamic instability) is necessary for their function as a mechanism to transport other cellular components. For example, during mitosis, microtubules position the chromosomes all through their replication and subsequent separation into the two daughter-cell nuclei. Furthermore, paclitaxel induces programmed cell death (apoptosis) in cancer cells by binding to the apoptosis stopping protein Bcl-2 (B-cell leukemia 2) and thus arresting its function.

Another group of DNA-interacting drugs widely used in anti-cancer chemotherapy is the group of anthracycline antibiotics which includes, inter alia, daunorubicin, doxorubicin (also known as Adriamycin® and doxorubicin hydrochloride), respinomycin D and idarubicin. These drugs interact with DNA by intercalation and inhibition of macromolecular biosynthesis thereby inhibiting the progression of the enzyme topoisomerase II, which unwinds DNA for transcription. They stabilize the topoisomerase II complex after it has broken the DNA chain for replication, preventing the DNA double helix from being rescaled and thereby stopping the process of replication. It is commonly used in the treatment of a wide range of cancers.

Alkylating antineoplastic agents directly attack DNA. They attach an alkyl group to DNA, cross-linking guanine nucleobases in DNA double-helix strands. This makes the strands unable to uncoil and separate. As this is necessary in DNA replication, the cells can no longer divide. These drugs act nonspecifically. Cyclophosphamide is an alkylating agent, however, it is a highly potent immunosuppressive substance.

Topoisomerase I and II inhibitors interfere with the enzymatic activity of topoisomerase I and 2, respectively, eventually leading to inhibition of both DNA replication and transcription. Examples of topoisomerase I inhibitors include topotecan and irinotecan. Irinotecan, is a prodrug converted to a biologically active metabolite 7-ethyl-10-hydroxy-camptothecin (SN-38) by a carboxylesterase-converting enzyme. One thousand-fold more potent than its parent compound irinotecan, SN-38 inhibits topoisomerase I activity by stabilizing the cleavable complex between topoisomerase I and DNA, resulting in DNA breaks that inhibit DNA replication and trigger apoptotic cell death. Because ongoing DNA synthesis is necessary for irinotecan to exert its cytotoxic effects, it is also classified as an S-phase-specific agent. Examples of topoisomerase II inhibitors include etoposide and teniposide.

Anti-angiogenic agents interfere with the generation of new blood vessels, eventually leading to the "starvation" of tumors. Non-limiting examples of anti-angiogenic agents include the monoclonal antibody bevacizumab, dopamine and tetrathiomolybdate.

Vascular endothelial growth factor (VEGF) is a 32-42 kDa dimeric glycoprotein which mediates vasodilatation, increased vascular permeability and endothelial cell mitogenesis. Differential exon splicing of the VEGF gene results in three main mRNA species which code for three secreted isoforms (subscripts denote numbers of amino acids): VEGF189, VEGF165, and VEGF121. A number of minor splice variants have also been described (VEGF206, VEGF183, VEGF145 and VEGF148). Variants of VEGF polypeptides and their use in cancer therapy is disclosed for example, in WO/2003/012105.

According to various embodiments, the at least one chemotherapeutic agent is selected from the group consisting of: antimetabolites, platinum-based drugs, mitotic inhibitors, anthracycline antibiotics, topoisomerase inhibitors, anti-angiogenic agents and combinations thereof.

According to some embodiments, the at least one chemotherapeutic agent is an antimetabolite, including purine antagonists, pyrimidine antagonists and folate antagonists. According to some embodiments, the antimetabolite is a pyrimidine antagonist. According to some embodiments, the antimetabolite is selected from the group consisting of: methotrexate, pemetrexed, cladribine, clofarabine, fludarabine, 6-mercaptopurine, nelarabine, pentostatin, capecitabine, cytarabine, 5-fluorouracil, uracil mustard, uracil, gemcitabine, hydroxyurea and fludarabine.

According to some embodiments, the at least one chemotherapeutic agent is a platinum-based drug including but not limited to cisplatin, carboplatin and oxaliplatin.

According to yet other embodiments, the at least one chemotherapeutic agent is a mitotic inhibitor including but not limited to paclitaxel, docetaxel, etoposide, vinblastine, vincristine and vinorelbine.

According to yet other embodiments, the at least one chemotherapeutic agent is an anthracycline antibiotic including but not limited to daunorubicin, respinomycin D and idarubicin.

According to some embodiments, the at least one chemotherapeutic agent is an anti-angiogenic agent including but not limited to bevacizumab, dopamine, tetrathiomolybdate, and antiangiogenic variants of VEGF.

According to some embodiments, the at least one chemotherapeutic agent is a topoisomerase inhibitor including but not limited to daunorubicin, doxorubicin, epirubicin, irinotecan, topotecan, etoposide and mitoxantrone.

According to some embodiments, the at least one chemotherapeutic agent is an alkylating agent including but not limited to carmustine, lomustine, bendamustine, dacarbazine and procarbazine.

Brachytherapy

According to yet another embodiment there is provided combined cancer therapy comprising the mAb of the invention and radiation treatments. Radiation is administered in accordance with well known standard techniques using standard equipment manufactured for this purpose, such as AECL Theratron and Varian Clinac.

The distance between the source of the external radiation and the point of entry into the patient may be any distance that represents an acceptable balance between killing target cells and minimizing side effects. Typically, the source of the external radiation is between 70 and 100 cm from the point of entry into the patient.

The source of radiation that may be used in combination with the mAb of the invention and the chemotherapeutic agent(s) can be either external or internal to the patient being treated. When the source is external to the patient, the therapy is known as external beam radiation therapy (EBRT). When the source of radiation is internal to the patient, the treatment is called brachytherapy (BT).

Brachytherapy is generally carried out by placing the source of radiation in the patient. Typically, the source of radiation is placed approximately 0-3 cm from the tissue being treated. Known techniques include interstitial, intercavitary, and surface brachytherapy. The radioactive seeds can be implanted permanently or temporarily. Some typical radioactive atoms that have been used in permanent implants include iodine-125 and radon. Some typical radioactive atoms that have been used in temporary implants include radium, cesium-137, and iridium-192. Some additional radioactive atoms that have been used in brachytherapy include americium-241 and gold-198.

The dose of radiation depends on numerous factors as is well known in the art. Such factors include the organ being treated, the healthy organs in the path of the radiation that might inadvertently be adversely affected, the tolerance of the patient for radiation therapy, and the area of the body in need of treatment. The dose will typically be between 1 and 100 Gy, and more particularly between 2 and 80 Gy. Some doses that have been reported include 35 Gy to the spinal cord, 15 Gy to the kidneys, 20 Gy to the liver, and 65-80 Gy to the prostate. It should be emphasized, however, that the invention is not limited to any particular dose. The dose will be determined by the treating physician in accordance with the particular factors in a given situation, including the factors mentioned above.

The dose of radiation for brachytherapy can be the same as that mentioned above for external beam radiation therapy. In addition to the factors mentioned above for determining the dose of external beam radiation therapy, the nature of the radioactive atom used is also taken into account in determining the dose of brachytherapy.

In another embodiment the anti-cancer treatment is a heparanase inhibitor, including but not limited to, glycol-split heparin compounds (e.g., Roneparstat).

In various embodiments of the combination methods of the invention, the mAb and the at least one drug or treatment (e.g., chemotherapy, radiation therapy) may be administered according to any of a number of treatment schedules, also referred to "dosing schedules" and "administration regimens", referring to the frequency of administration and order of administration of each active agent. For example, the mAb and the at least one chemotherapeutic agent may be administered substantially simultaneously i.e. at the same time, using for example a combined dosage form or separate dosage forms. This form of administration may also be referred to as "concomitant" administration. Concurrent administration refers to administration of the active agents within the same general time period, for example on the same day(s) but not necessarily at the same time. For example, one active agent may require administration with food, while the other requires administration in the semi-fasting state. Alternate administration includes administration of one agent during a particular time period, for example over the course of a few days or a week, followed by administration of the other agent during a subsequent identical period of time, and then repeating the pattern for one or more cycles. Sequential or successive administration includes administration of one agent during a first time period, using one or more doses, followed by administration of the other agent during a second time period using one or more doses. An overlapping schedule may also be employed, which includes administration of the active agents on different days over the treatment period, not necessarily according to a regular sequence. Variations on these general guidelines may also be employed, according to the agents used and the condition of the subject.

Proteasome Inhibitor

According to yet another embodiment there is provided combined cancer therapy comprising the mAb of the invention and a proteasome inhibitor. A proteasome inhibitor is a drug that blocks proteasomes. Proteasomes are enzymes which degrade unneeded or damaged proteins.

In some embodiments the proteasome inhibitor comprises Bortezomib, Carfilzomib, Ixazomib, or a combination thereof. In some embodiments the proteasome inhibitor is Bortezomib.

Methods of the Invention

The mAbs of the invention are useful for treating a disease or disorder associated with heparanase activity in a subject in need thereof. In some embodiments there is provided use of the mAbs of the invention for preparation of a medicament for treating a disease or disorder associated with heparanase activity.

As used herein, the terms "heparanase activity", "heparanase enzymatic activity" or "heparanase catalytic activity" refer to an animal endoglycosidase hydrolyzing activity which is specific for heparin or heparan sulfate substrates, as opposed to the activity of bacterial enzymes (heparanase I, II and III) which degrade heparin or heparan sulfate by means of beta-elimination.

Heparanase activity which is inhibited or neutralized according to the present invention can be of either recombinant or natural heparanase. Such activity is disclosed, for example, in U.S. Pat. Nos. 6,177,545 and 6,190,875, which are incorporated by reference as if fully set forth herein. Methods for determining heparanase activity as well as antibodies neutralizing effect are known in the art. In some embodiments, heparanase neutralizing effect may be measured by activity assays as described herein (e.g., Example 1 and 3). In another embodiments, the affinity of an antibody to a the heparan sulfate (HS) binding domain, such as the $Lys^{158}$-$Asp^{171}$ domain of human heparanase may be measured. In additional embodiments, the cellular uptake of heparanase may be measured.

As used herein, the term "associated with heparanase catalytic activity" refers to conditions which at least partly depend on the catalytic activity of heparanase. It is being understood that the catalytic activity of heparanase under many such conditions can be normal, yet inhibition thereof in such conditions will result in improvement of the affected individual.

The pharmaceutical composition according to the present invention may be administered as a stand-alone treatment or in addition to a treatment with any other therapeutic agent. According to a specific embodiment, antibodies according to the present invention are administered to a subject in need thereof as part of a treatment regimen in conjunction with at least one anti-cancer agent. The pharmaceutical composition according to the present invention may be administered together with other agents or separately.

As used herein to describe the present invention, "malignant proliferative disorder" "cancer", "tumor" and "malignancy" all relate equivalently to a hyperplasia of a tissue or organ. All types of tumors may be treated by the methods of the present invention. The tumors may be solid or non-solid.

According to some embodiments, the mAb of the invention or a composition comprising the same, can be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma.

According to another embodiment, the proliferative disease is a solid malignancy including but not limited to carcinoma, sarcoma, glioma and melanoma. According to additional embodiments, the mAb of the invention or a composition comprising the same, can be used for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extrahepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

It is to be therefore understood that the compositions of the invention are useful for treating or inhibiting tumors at all stages, namely tumor formation, primary tumors, tumor progression or tumor metastasis.

In another embodiment, mAb of the invention can be used for inhibition of angiogenesis, and are thus useful for the treatment of diseases and disorders associated with angiogenesis or neovascularization such as, but not limited to, tumor angiogenesis, opthalmologic disorders such as diabetic retinopathy and macular degeneration, particularly age-related macular degeneration, and reperfusion of gastric ulcer.

The mAb of the invention or any compositions thereof are useful for inhibiting or treating other cell proliferative diseases or disorders such as psoriasis, hypertrophic scars, acne and sclerosis/scleroderma, and for inhibition or treatment of other diseases or disorders such as polyps, multiple exostosis, hereditary exostosis, retrolental fibroplasia, hemangioma, and arteriovenous malformation.

Heparanase catalytic activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of heparan sulfate (HS) by heparanase catalytic activity (Vlodavsky, I. et al., Invasion & Metastasis 12, 112-127 (1992)). The enzyme is released from intracellular compartments (e.g., lysosomes, specific granules) in response to various activation signals (e.g., thrombin, calcium ionophore, immune complexes, antigens, mitogens), suggesting its regulated involvement and presence in inflammatory sites and autoimmune lesions. Heparanase released by platelets and macrophages is likely to be present in atherosclerotic lesions (Campbell, K. H. et al. Exp. Cell Res. 200, 156-167 (1992)). Thus, the mAb of the invention or any compositions thereof are also useful for inhibiting or treating autoimmune and inflammatory diseases.

Therefore, in another embodiment, the compositions of the invention may be useful for treatment of or amelioration of inflammatory symptoms in any disease, condition or disorder where immune and/or inflammation suppression is beneficial such as, but not limited to, treatment of or amelioration of inflammatory symptoms in the joints (Li et al. Arthritis Rheum 2008, 58:1590-600), musculoskeletal and connective tissue disorders, or of inflammatory symptoms associated with hypersensitivity (Edovitsky et al. Blood 2005, 3609-16) allergic reactions, asthma, atherosclerosis (Planer et al. Plos ONE 2011; 6(4): e18370), otitis and other otorhinolaryngological diseases, dermatitis and other skin diseases, posterior and anterior uveitis, conjunctivitis, optic neuritis, scleritis and other immune and/or inflammatory ophthalmic diseases.

In another embodiment, the compositions of the invention are useful for treatment of or amelioration of an autoimmune disease such as, but not limited to, Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM), systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis (Li et al. Arthritis Rheum 2008, 58:1590-600), scleroderma, thrombocytopenia, thyroiditis e.g. Hashimoto's disease, Sjbgren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behget's syndrome, ankylosing spondylitis, pemphigus, bullous pernphigoid, dennatitis herpetiformis, insulin dependent diabetes, inflammatory bowel disease, ulcerative colitis and Crohn's disease (Lerner et al, J Clin Invest 2011, 121:1709-21).

Still further, heparanase has been proposed to be involved in the pathogenesis of proteinuria by selectively degrading the negatively charged side chains of heparan sulfate proteoglycans within the glomerular basement membrane. A loss of negatively charged heparan sulfate proteoglycans may result in alteration of the permselective properties of the glomerular basement membrane, loss of glomerular epithelial and endothelial cell anchor points, and liberation of growth factors and potentially leading to different kidney disorders, such as, passive Heymann nephritis (PHN), and puromycin aminonucleoside nephrosis (PAN). As described by Levidiotis, V. et al. (Levidiotis, V. et al., J. Am. Soc. Nephrol. 15, 68-78 (2004)), a polyclonal antibody against heparanase, significantly reduced proteinuria without affecting the histologic appearance of glomeruli and the immune mechanisms, which give rise to PHN, and therefore, inhibition of heparanase may be used to reduce proteinuria. Notably, the heparanase inhibitor Roneparstat reduced proteinuria associated with type 1 and type 2 diabetes (Gil et al. Diabetes 2012; 61:208-16). Therefore, in another embodiment, the compositions and mAbs as described herein are useful for treatment of or amelioration of any kidney disorder and organ fibrosis (Abassi and Goligorsky M S. Adv Exp Med Biol. 2020; 1221:685-702; van der Vlag and Buijsers. Adv Exp Med Biol. 2020; 1221:647-667; Masola et al., Adv Exp Med Biol. 2020; 1221:669-684).

In another embodiment, the compositions and mAbs as described herein are useful for treatment of or amelioration of diabetic nephropathy. In another embodiment, the compositions and mAbs as described herein are useful for treatment of or amelioration of type-1 diabetes (Ziolkowski et al. 2012; 122:132-41, Simeonovic et al., Adv Exp Med Biol. 2020; 1221:607-630).

In another embodiment, the compositions and mAbs as described herein are useful for treatment of or amelioration of amyloidosis (Li J P and Zhang X. Adv Exp Med Biol. 2020; 1221:631-645), and of viral infections (Agelidis A, Shukla D. Adv Exp Med Biol. 2020; 1221:759-770). In another embodiment, the compositions and mAbs of the invention are useful for treatment of or amelioration of sepsis.

The term "mammal" means any mammal, including pet animals, such as dogs and cats; farm animals, such as pigs, cattle, sheep, and goats; laboratory animals, such as mice and rats; primates, such as monkeys, apes, and chimpanzees; and preferably, humans.

Having now generally described the invention, the same will be more readily understood through reference to the following examples, which are provided by way of illustration and are not intended to be limiting of the present invention.

EXAMPLES

Materials and Methods.

Generation of murine monoclonal antibodies (mAb). BALB/c mice were immunized with 50 μg of recombinant 65 kDa latent pro-heparanase coupled to Keyhole limpet hemocyanin (KLH) in complete Freund's adjuvant (CFA; Sigma), followed by five injections (50 µg) of KLH-heparanase in incomplete Freund's adjuvant (IFA) every 2 weeks. Following tail vein injection, splenocytes were isolated, fused with NSO myeloma cells, and hybridomas were screened for their ability to bind pro-heparanase by ELISA, essentially as described (Gingis-Velitski et al. Faseb J 2007; Levy-Adam et al. J Biol Chem 2010; 285 (36): 28010-9; Shafat et al. Biochem Biophys Res Commun 2006; 341(4): 958-63). Positive hybridomas were selected, expanded and cloned. Hybridoma subclass was determined by isotyping kit according to the manufacturer's (Serotec, Oxford, UK) instructions. mAb A54 was characterized as IgG1-Kappa and was purified by affinity chromatography on Protein G Sepharose 4 according to the manufacturer's (Pierce Biotechnology, Rockford, IL) instructions.

Purified mAb A54 antibody was resolved by SDS-PAGE, heavy and light chain protein bands were extracted and sequenced. The corresponding nucleotide sequences were then revealed, and the genes were amplified by RT-PCR and cloned. Briefly, Total RNA was isolated from the hybridoma cells using the TRIzol® reagent. It was then reverse transcribed into cDNA using isotype-specific antisense primers. The antibody fragments of VH and VL were amplified according to the standard rapid amplification of cDNA ends (RACE). The amplified antibody fragments were cloned into a standard cloning vector separately. Colony PCR was performed to screen for clones with inserts of correct sizes. No less than five colonies with inserts of correct sizes were sequenced for each fragment. The sequences of different clones were aligned, and the consensus nucleotide and amino acid sequences of these clones are provided in Table 1. Mouse IgG (Sigma) was used as control.

TABLE 1

| Nucleotide and amino acid sequences of mAb A54. | | | |
|---|---|---|---|
| Variable Chain | | Sequence | SEQ ID NO: |
| Variable Heavy Chain | Amino acid sequence | QVQLQQSGAELAKPGASVRMSCKASGYTFTN YWMHWVKQRPGQGLEWIGYINPTTGYTEYNQ KFKDKATLTADKSSSTAYMQLSSLTSEDSAVY YCARGGAGYDYDEDYAMDYWGQGTSVTVSS | 7 |
| | Nucleic acid sequence | CAAGTGCAGCTGCAGCAGAGCGGCGCCGAG CTGGCCAAGCCTGGCGCTTCTGTGCGGATGA GCTGCAAGGCCTCTGGCTACACCTTCACCAA CTACTGGATGCACTGGGTCAAGCAGAGACCT GGACAGGGCCTGGAATGGATCGGCTACATCA ACCCCACCACCGGCTACACGGAATACAACCA GAAGTTCAAGGACAAGGCCACACTGACAGC CGACAAAAGCAGCAGCACCGCCTACATGCA GCTGAGCAGCCTGACCAGCGAGGACAGCGC CGTGTACTACTGCGCCAGAGGCGGAGCCGGC TATGATTACGACGAGGATTACGCCATGGACT ACTGGGGCCAGGGTACAAGCGTGACCGTGTC CAG | 9 |
| | CDR-H1 | GYTFTN | 1 |
| | CDR-H1 | GYTFTNYWMH | 17 |
| | CDR-H1 | AACTACTGGATGCAC | 11 |
| | CDR-H2 | YINPTTGYTEYNQKFKD | 2 |
| | CDR-H2 | TACATCAACCCCACCACCGGCTACACGGAAT ACAACCAGAAGTTCAAGGAC | 12 |
| | CDR-H3 | GGAGYDYDEDYAMDY | 3 |
| | CDR-H3 | GGCGGAGCCGGCTATGATTACGACGAGGATT ACGCCATGGACTAC | 13 |
| Variable Light Chain | Amino acid sequence | DIVLTQSPASLAVSLGQRATISCRASESVEYFGT SYMNWYQQKPGQPPKLLIYLASILESGIPARFS GSGSGTDFTLNIHPVEEEDAATYYCQQSNEDP YTFGGGTKLEIK | 8 |
| | Nucleic acid sequence | GACATCGTGCTGACCCAGAGCCCTGCCTCTC TGGCCGTGTCCCTGGGCCAGCGGGCCACCAT CAGCTGCAGAGCCAGCGAGAGCGTGGAATA CTTCGGCACCAGCTACATGAACTGGTACCAG CAGAAACCTGGCCAGCCTCCTAAGCTGCTGA TCTACCTGGCTAGCATCCTGGAAAGCGGCAT CCCCGCCAGATTCAGCGGATCTGGCAGCGGC ACCGACTTCACCCTGAACATCCACCCCGTGG AAGAGGAAGATGCCGCCACATACTACTGCCA GCAATCTAATGAGGACCCCTACACCTTCGGC GGCGGAACAAAGCTGGAAATCAAG | 10 |
| | CDR-L1 | RASESVEYFGTSYMN | 4 |
| | CDR-L1 | AGAGCCAGCGAGAGCGTGGAATACTTCGGC ACCAGCTACATGAAC | 14 |
| | CDR-L2 | LASILES | 5 |
| | CDR-L2 | CTGGCTAGCATCCTGGAAAG | 15 |
| | CDR-L3 | QQSNEDPYT | 6 |
| | CDR-L3 | CAGCAATCTAATGAGGACCCCTACACC | 16 |

Cells and cell culture. Human HEK 293, U87-MG glioma, and CAG myeloma cells, and mouse 4T1 breast carcinoma, and MPC-11 myeloma cells were purchased from the American Type Culture Collection (ATCC, Manassas, VA). CAG myeloma (Ramani et al., Matrix Biol. 2016; 55:22-34), U87 glioma (Barash et al., Int J Cancer, 2019; 145 (6): 1596-1608) and 4T1 breast carcinoma (Hammond et al., PLOS One 2012; 7 (12): e52175) cells have been described previously. Cells were grown in Dulbecco's modified Eagle's medium (Biological Industries, Beit Haemek, Israel) supplemented with 10% fetal calf serum and antibiotics.

Cell lysates, heparanase activity and protein blotting. Preparation of cell lysates, protein blotting, and measurement of heparanase enzymatic activity were carried out as described (Arvatz et al. Faseb J 2011; 24 (12): 4969-76). For inhibition studies, highly purified recombinant heparanase (200 ng) was pre-incubated with the indicated antibody (2 µg) for 30 min on ice under neutral pH conditions (pH 7.2) before being added to 35S-labelled ECM, used as a naturally produced substrate for heparanase (Gingis-Velitski et al. 2007, ibid.).

ECM degradation assay. The extracellular matrix (ECM) substrate is deposited by cultured endothelial cells and hence closely resembles the subendothelial basement membrane in its composition, biological function and barrier properties. Years of experience indicate that compounds that effectively inhibit the enzyme in this assay are also effective in preclinical animal models. More detail about the preparation of this substrate and its use for the heparanase assay can be found in: Current Protocols in Cell Biology (Vlodavsky 2001; pp. 10.4.1-10.4.14). Briefly, sulfate [$^{35}$S] labeled ECM coating the surface of 35 mm tissue culture dishes, is incubated (4 h, 37° C., pH 6.0, 1 ml final volume) with recombinant human heparanase (200 ng/ml) in the absence and presence of the A54 mAb. The reaction mixture contains: 50 mM NaCl, 1 mM DTT. 1 mM CaCl2, and 10 mM buffer Phosphate-Citrate, pH 6.0. To evaluate the occurrence of proteoglycan degradation, the incubation medium is collected and applied for gel filtration on Sepharose 6B columns (0.9×30 cm). Fractions (0.2 ml) are eluted with PBS and counted for radioactivity. The excluded volume (Vo) is marked by blue dextran and the total included volume (Vt) by phenol red. Degradation fragments of HS side chains are eluted from Sepharose 6B at 0.5<Kav<0.8 (peak II). Results are best represented by the actual gel filtration pattern (vlodavsky et al., Nature Med. 5:793-802, 1999).

Matrigel invasion assay. Invasion assay was performed using modified Boyden chambers with polycarbonate Nucleopore membrane, essentially as described (Arvatz et al. 2011, ibid.). Briefly, filters (6.5 mm in diameter, 8 µm pore-size) were coated with Matrigel (30 µl); Cells (2×10$^5$) in 100 µl of serum-free medium were seeded in triplicate on the upper part of each chamber in the presence of the indicated antibody, and the lower compartment was filled with 600 µl medium supplemented with 10% FCS. After incubation for 5 h at 37° C. in a 5% $CO_2$ incubator, non-invading cells on the upper surface of the filter were wiped with a cotton swab, and migrated cells on the lower surface of the filter were fixed, stained with 0.5% crystal violet (Sigma) and counted by examination of at least seven microscopic fields (Barash et al., J Natl Cancer Inst. 110: 1102-1114, 2018).

Tumorigenicity

U87 glioma. Cells from exponential cultures of Luciferase labeled U87 glioma cells were detached with trypsin/

EDTA, washed with PBS and brought to a concentration of 5×10$^7$ cells/ml. Cell suspension (5×10$^6$/0.1 ml) was inoculated subcutaneously at the right flank of 5-weeks old female SCID/Beige mice (n=7). Three days after cell inoculation, mice are randomly assigned to 2 cohorts (5-10 mice each) receiving (a) vehicle (PBS); and (b) A54 mAb (500 µg/mouse, 3 times/week). Tumor development is inspected (once a week) by IVIS imaging following administration of luciferin (see below) as described (Barash et al. FASEB J 2010; 24:1239-48, Barash et al., J Natl Cancer Inst. 110: 1102-1114, 2018). At the end of the experiment, mice are sacrificed, and xenografts are resected, weighted and fixed in formalin for pathological examination.

4T1 mouse breast carcinoma (Experimental metastasis). Luciferase labeled 4T1 breast carcinoma cells (1×10$^5$/Balb/c mouse) are injected i.v (n=10 mice/group; 2 groups: untreated control, A54 mAb). Antibodies are injected (i.p, 500 µg/mouse, 3 times/week) 20 min prior to cell inoculation. IVIS bioluminescent imaging is performed 6, 10 and 14 days after cell inoculation. At termination, mice are sacrificed and the lungs subjected to pathological examination and counting of cell colonies per 5 microscopic fields. The cells metastasize primarily to the lungs and the luminescent signal is reproducible, quantitative, and reliable.

4T1 mouse breast carcinoma (spontaneous metastasis). Luciferase labeled 4T1 breast carcinoma cells (1×10$^5$/Balb/c mouse) are injected directly into the third mammary fat pad and treatment of mice (PBS control vs. mAb A54 500 µg/mouse, 3 times/week began 3 days after 4T1 cell inoculation. Mice were randomized into two groups of 6 mice, 4 days postinoculation (Day 0). On day 15 of the study the mammary fat pad including the primary tumor was excised on all mice while under 2% Isoflurane anaesthetic. Mice were treated with mAb A54 as described above and IVIS bioluminescent imaging is performed 12 and 18 days after mastectomy. At termination, mice are sacrificed and the number of overt macrometastases on the surface of the lungs was enumerated manually (Hammond et al., PLOS One 2012; 7 (12): e52175).

CAG myeloma. Luciferase-labeled CAG human myeloma cells (5×10$^6$) are injected into the tail vein of NOD/SCID mice. Three days after cell inoculation, mice are randomly assigned to 2 cohorts (5-10 mice each) receiving (a) vehicle (PBS); and (b) A54 mAb (500 µg/mouse, 3 times/week). Tumor development is inspected (once a week) by IVIS imaging following administration of luciferin (see below). At termination, mice are sacrificed the backbones are excised, fixed in formalin and following de-calcification with 10% EDTA solution are embedded in paraffin and subjected to histological and immunohistochemical analyses.

MPC-11 myeloma. Mouse MPC-11 myeloma cells are detached with trypsin/EDTA, washed with PBS, brought to a concentration of 5×10$^5$ cells/0.2 ml and inoculated subcutaneously at the right flank of 6-8-weeks-old Balb/c mice. Three days after cell inoculation, mice are randomly assigned to 2 cohorts (6 mice each) receiving (a) vehicle (PBS); and (b) A54 mAb (500 µg/mouse, 3 times/week. Xenograft size is determined on day 7, 10 and 14 by externally measuring tumors in 2 dimensions using a caliper. At the end of the experiment, mice are sacrificed and tumor xenografts are removed and weighed.

B16 melanoma. B16-BL6 mouse melanoma cells (2×10$^5$) were injected into the tail vein of C57/BL mice together with the indicated compound and lung metastases was determined 18 days thereafter. All animal experiments were approved by the Animal Care Committee of the Technion, Haifa, Israel.

IVIS imaging. Bioluminescent imaging of luciferase-expressing tumors is performed with a highly sensitive, cooled charge coupled device (CCD) camera mounted in a light-tight specimen box (IVIS; Xenogen Corp., Waltham, MA). Imaging is performed in real time, is non-invasive and provides quantitative data. Briefly, mice are injected intra-peritoneally with D-luciferin substrate at 150 mg/kg, anesthetized and placed onto a warmed stage inside the light-tight camera box, with continuous exposure to isoflurane (EZAnesthesia, Palmer, PA). Light emitted from the biolu-minescent cells is detected by the IVIS camera system with images quantified for tumor burden using a log-scale color range set at $5\times10^4$ to $1\times10^7$ and measurement of total photon counts per second (PPS) using Living Image software (Xenogen).

Statistics. Data are presented as mean±SE. Statistical significance was analyzed by two-tailed Student's t-test. The value of $P<0.05$ is considered as significant.

Example 1. Identification and Selection of the Most Active Heparanase-Neutralizing Monoclonal Antibody In order to select the hybridoma clone that best inhibits heparanase enzymatic activity, supernatants of the various hybridomas, raised against the 65 kDa latent heparanase protein, were collected, pre-incubated with recombinant heparanase and examined for the capacity to inhibit the release of heparan sulfate (HS) degradation fragments from sulfate labeled ECM. For this purpose, purified recombinant active heparanase (200 ng) was pre incubated with the various hybridoma supernatants for 2 h in serum-free RPMI medium on ice. The mixture was then applied onto 35S-labeled ECM-coated dishes and heparanase activity was determined as described under "Materials and Methods" above. As shown in FIG. 1, pre-incubation with hybridoma #A54 yielded the best heparanase inhibitory activity (nearly 80% decrease in the amount of released sulfate labeled HS degradation products) as compared to all the other hybridoma supernatants.

Example 2. mAb A54 Preferentially Recognizes Heparanase

An ELISA method was applied to characterize the pref-erential recognition of heparanase by mAb A54 vs. control mouse IgG (FIG. 2A). For this purpose, microtiter 96-well plate was coated with latent 65 kDa heparanase (Hpa65). Purified (protein G Sepharose) mAb A54 or control mouse IgG were then added at the indicated concentrations and the extent of binding to the immobilized heparanase was deter-mined by ELISA. While there was no interaction with non-immune mouse IgG, the A54 antibody exhibited a high affinity binding to the enzyme (IC50=0.45 nM). Next, the purified A54 mAb was subjected SDS-PAGE (FIG. 2B) and Western blot (FIG. 2C, Secondary antibody: Goat Anti-Mouse Kappa-HRP) analyses to further characterize the purity, molecular weight and isotype of the antibody light and heavy chains. Lanes M1 and M2: Protein Marker; Lane 1: Reducing condition; Lane 2: Non-reducing condition; Lane P: Mouse IgG1, Kappa as a positive control. (Ab: antibody: Goat Anti-Mouse IgG-HRP). Briefly, mAb A54 was expressed in 293F cells applying the pcDNA3.4 expression vector and serum free (Expi293F) medium. The anti-body isotype was characterized as IgG1-Kappa.

Example 3. mAb A54 Inhibits Heparanase Enzymatic Activity

Next, the ability of purified mAb A54 to inhibit hepara-nase enzymatic activity was examined. For this purpose, recombinant active heparanase (200 ng) was preincubated with control mouse IgG or purified mAb A54 (0.1 and 1 μg/ml) for 1 h in serum-free RPMI medium on ice. The mixture was then applied onto dishes coated with 35S-labeled ECM, and heparanase enzymatic activity was deter-mined as described in 'Methods'. As shown in FIG. 3B, preincubation with 0.1 μg/ml of the antibody yielded nearly 75% inhibition of the enzyme and complete inhibition (i.e., release of HS degradation fragments eluted in fractions #15-30 when subjected to gel filtration on Sepharose 6B) was obtained in the presence of 1 μg/ml of the antibody, as shown in FIG. 3A. There was no inhibitory effect to non-immune mouse IgG.

Example 4. mAb A54 Attenuates Cell Invasion

Thereafter, the antibody effect on cell invasion was exam-ined. Briefly, U87 glioma cells ($1\times10^5$) were plated onto Matrigel-coated 8-μm Transwell filters in the presence of control mouse IgG or mAb A54 (2 μg). Invading cells adhering to the lower side of the membrane were visualized after 6 h (FIGS. 4A-B) and quantified (FIG. 4C; number of invading cells per high power field; *p=0.001) as described in 'Methods'. As demonstrated in FIGS. 4A-C, invasion of U87 glioma cells through Matrigel (reconstituted basement membrane) was attenuated by nearly 90% in the presence mAb A54.

Example 5. Anti-Heparanase mAb A54 Attenuates Human Myeloma and Glioma Tumor Growth The ability of mAb A54 to attenuate myeloma tumor development over time was examined. Briefly, NOD/SCID mice (n=5) were inoculated intravenously (i.v.) with Luc-CAG human myeloma cells ($5\times10^6$) and the mice were treated with A54 mAb (500 μg/mouse, 3 times/week) or PBS as control, starting on day 3 following cell inoculation. Tumor growth was evaluated 3 weeks later by IVIS imaging (FIGS. 5A and 5B). Quantification of luciferase signals is also shown graphically (FIG. 5C). As demonstrated in FIG. 5B, a marked reduction in the myeloma growth rate was noted (P=0.02).

Similarly, Luc-U87 human glioma cells ($5\times10^6$/0.1 ml) were inoculated subcutaneously (s.c.) at the right flank of 5-weeks old female NOD/SCID mice (n=5). Mice were treated with mAb A54 (500 μg/mouse, 3 times/week) or PBS as control. Tumor growth was evaluated by IVIS imaging (FIGS. 5D and 5E) and quantification of luciferase signals is shown graphically (FIG. 5F). As shown in FIG. 5E, a marked inhibition of the glioma tumor growth rate was noted in the antibody treated mice (P=0.04).

Example 6. Anti-Heparanase mAb A54 Attenuates Mouse Myeloma Tumor Growth

Figure 6A:
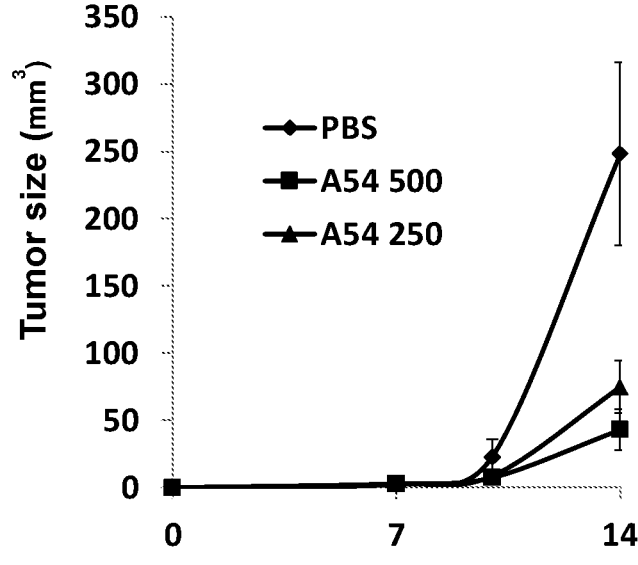
Figure 6B:
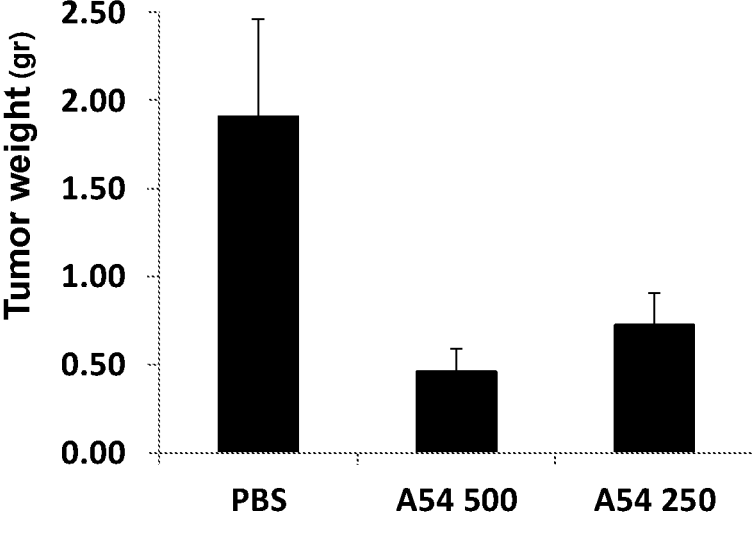

Having demonstrated the inhibitory effect of mAb A54 in immunocompromised mouse model, the effect of the anti-body in a syngeneic (immuno-competent) mouse model was examined next. Briefly, Balb/c mice were inoculated (s.c.)

with MPC-11 mouse myeloma cells ($0.5\times10^6$). Treatment with mAb A54 (250 or 500 μg/mouse every other day) was initiated two days after cell inoculation. Control cells were administrated with PBS. Xenograft size was determined twice a week by externally measuring the tumors in two dimensions using a caliper, and tumor volume was calculated (FIG. 6A). At the end of the experiment (Day 14) xenografts were removed, weighed (FIG. 6B), fixed in formalin and photographed (FIG. 6C). The results indicate that treatment with mAb A54 markedly attenuated (4-fold) myeloma tumor growth and that the higher dose of antibody was more effective. The above results imply that the development of primary tumors can be restrained by the anti-heparanase mAb A54.

Example 7. MAb A54 Attenuates Mouse Breast Carcinoma Spontaneous Metastasis

Figure 7C:
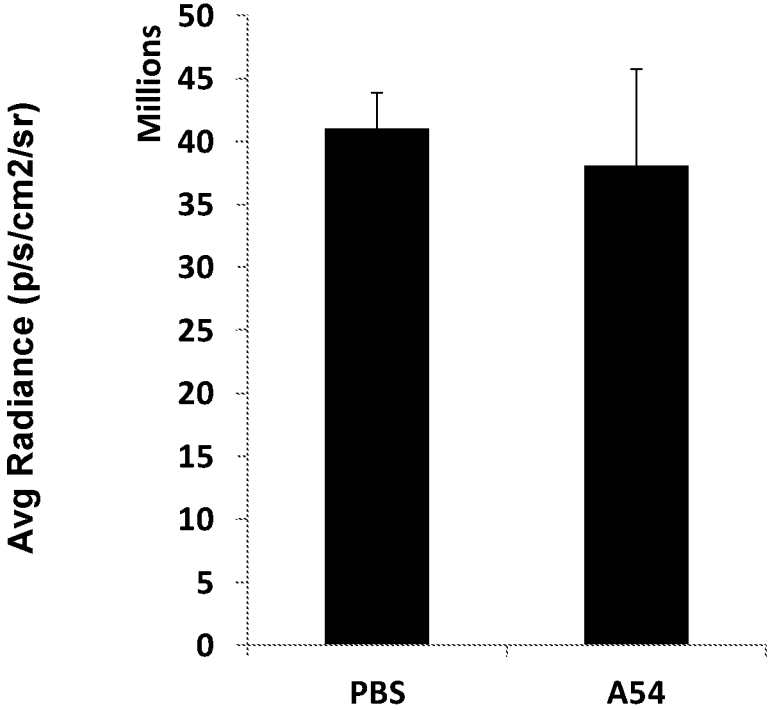
FIG. 7C is a bar graph representing quantification of
the respective luciferase signals.
Figure 7G:
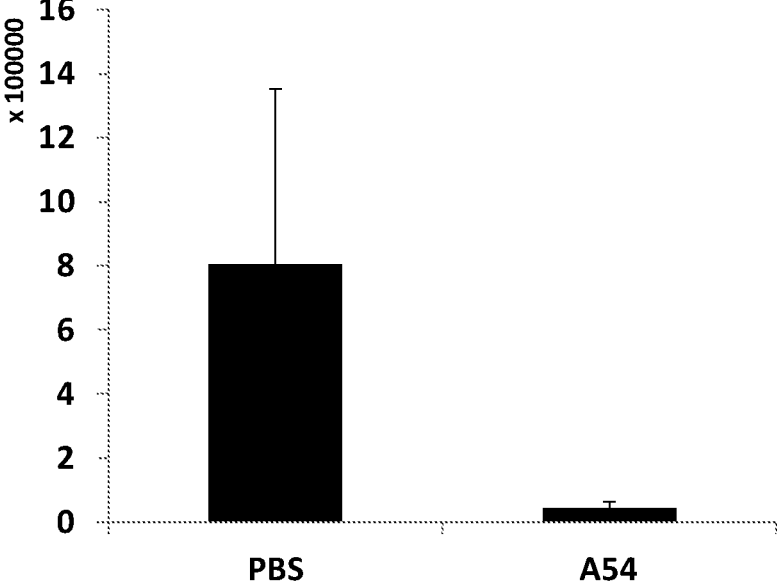
FIG. 7G is
a bar graph representing quantification of the respective
luciferase signals.

In subsequent studies, the effect of mAb A54 on cancer metastasis, the hallmark of heparanase activity, was investigated. A syngeneic breast carcinoma model was applied, which resembles the scenario in humans. Briefly, luciferase labeled 4T1 breast carcinoma cells ($0.5\times10^5$) were orthotopically injected into the third mammary fat pad of Balb/c mice. Treatment of the mice (PBS control vs. mAb A54; 500 μg/mouse, 3 times/week) began 3 days after 4T1 cell inoculation. IVIS imaging performed on day 12 revealed no differences in the luciferase signal generated by the primary tumors (FIGS. 7A and 7B). On day 15 of the study the mammary fat pad including the primary tumor was excised from all mice (under 2% Isoflurane anesthetic) and weighed. There was no difference in weights between tumors derived from A54-treated and untreated mice (FIG. 7C). Mice were further treated with mAb A54 as described above and IVIS bioluminescent imaging was performed on day 35 (e.g., 23 days after mastectomy). As demonstrated in FIGS. 7E and 7F, only two out of the 5 untreated mice developed lung metastases as compared to a hardly-detected signal revealed in the A54 treated mice (one mouse died on day 15 of the experiment). The experiment was repeated with similar results, further indicating an almost complete inhibition of lung colonization in this model system.

Figures 8A, 8C:
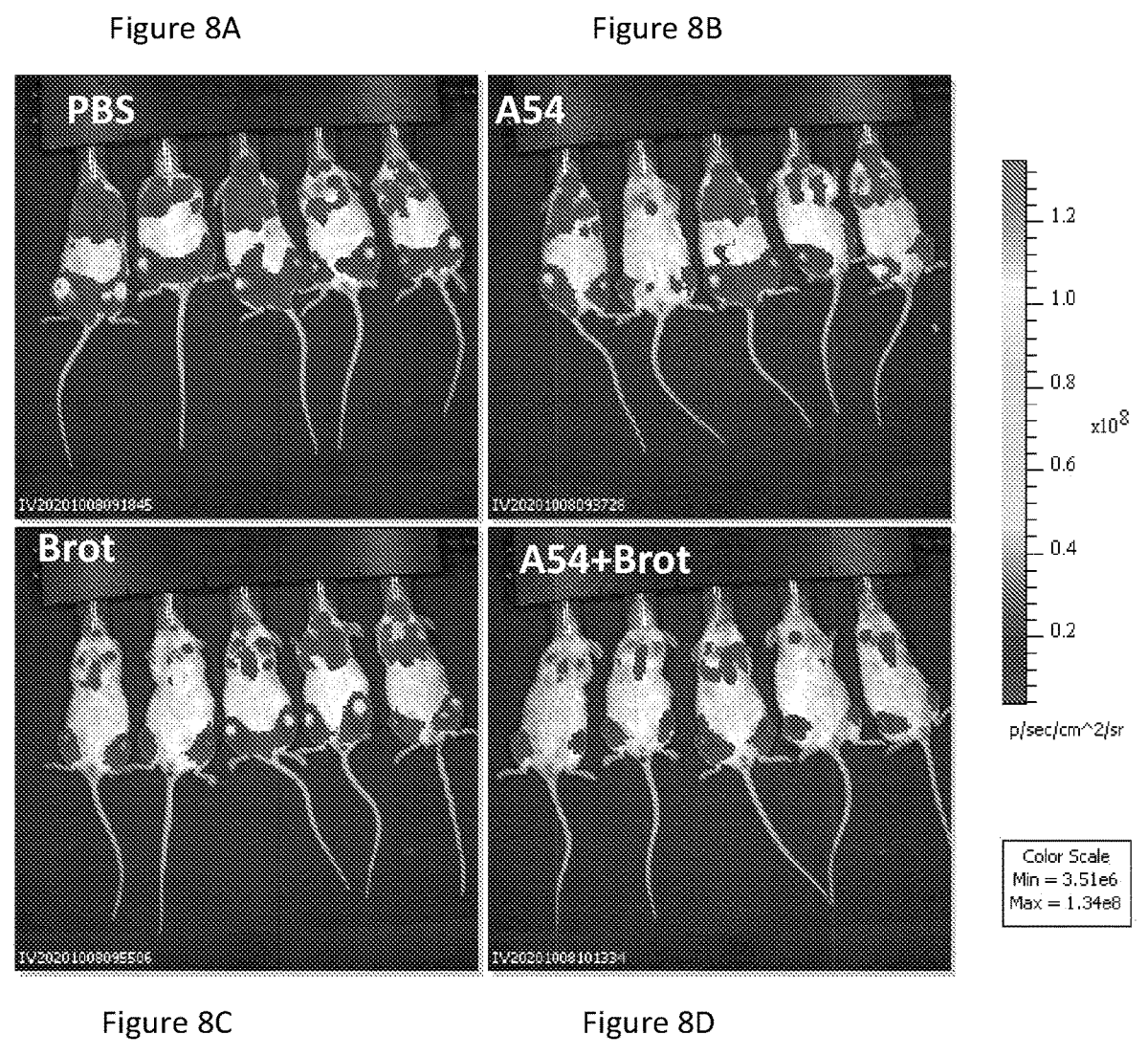

Example 8. Combination of A54 mAb and Bortezomib Attenuate Myeloma Tumor Growth In subsequent studies, the effect of mAb A54 in combination with bortezomib on myeloma tumor growth, was investigated. NOD/SCID mice (n=5) were inoculated (i.v.) with CAG luciferase cells ($5\times10^6$), and mice were treated with A54 mAb (360 μg/mouse, 2 times/week) or Brotezomib (Brot; 0.5 mg/kg twice a week) or A54 mAb+Brotezomib (as noted) or PBS as control. Tumor growth was evaluated by IVIS imaging (FIGS. 8A-D) and quantification of luciferase signals is shown graphically (FIG. 8E). The results indicate that treatment of myeloma by a combination of A54 mAb and bortezomib attenuates the tumor growth.

Example 9. A54 mAb Attenuates Breast Carcinoma Tumor Growth

Figure 9C:
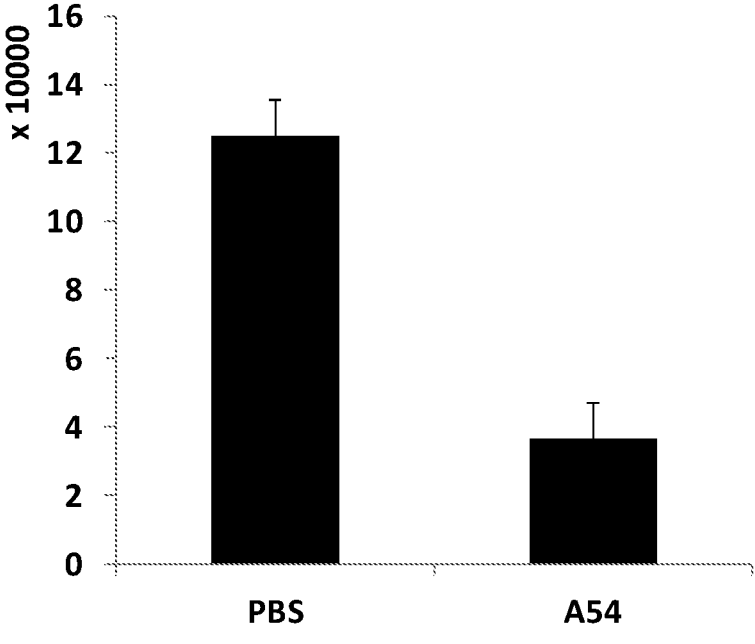
FIG. 9C is a bar graph representing quantification of
the respective luciferase signals.
Figure 9D:
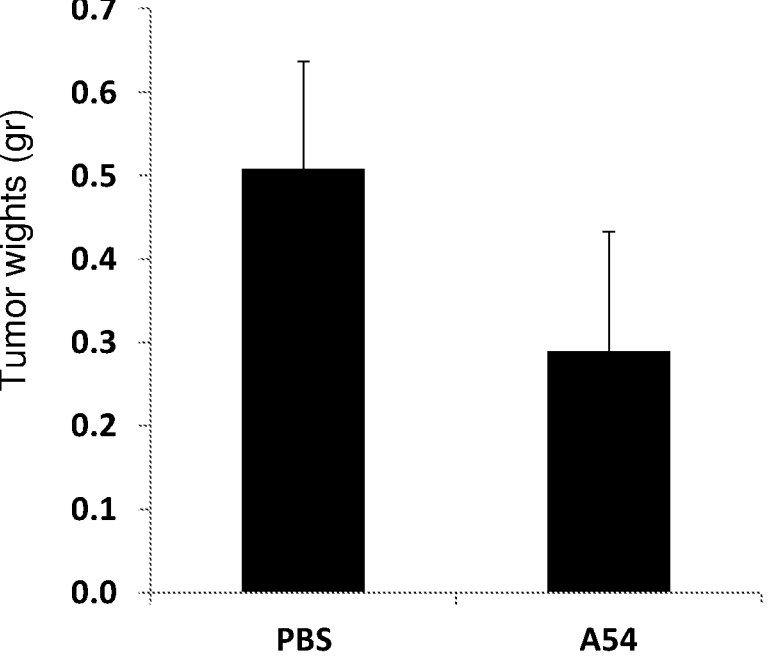
FIG. 9D is a bar graph
representing the weights of tumors excised from Balb/c mice
treated with vehicle (PBS) or with mAb A54 as described in
FIGS. 9A and 9B.

In subsequent studies, the effect of mAb A54 on breast carcinoma tumor growth was investigated. Balb/c mice (n=3) were inoculated in the mammary fad pad with EMT-6 luciferase cells ($0.5\times10^6$), and mice were treated with A54 mAb (360 μg/mouse, 2 times/week) or PBS as control. Tumor growth was evaluated by IVIS imaging (FIGS. 9A and 9B) and quantification of luciferase signals is shown graphically (FIG. 9C). At the end of the experiment, tumors were resected and weighted (FIG. 9D). The results indicate that A54 mAb treatment attenuates the growth of breast carcinoma.

Example 10. A54 mAb Effectively Protects Mice from LPS-Induced Sepsis

Figure 10:
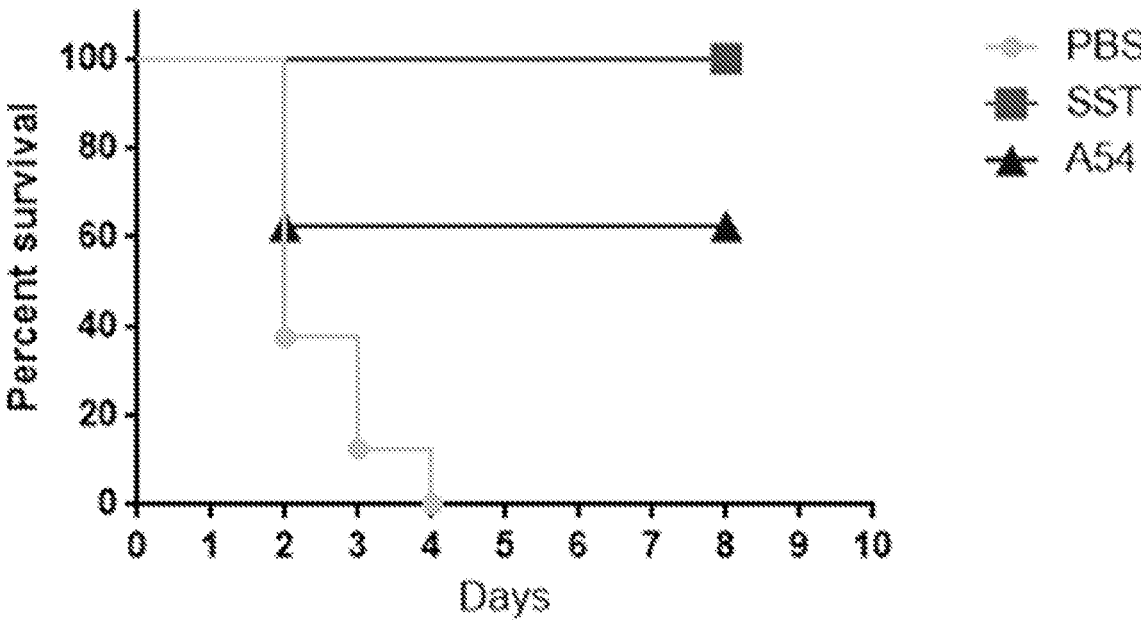
FIG. 10 is a line graph representing survival of C57BL/6
mice treated with A54 mAb, Roneparstat or PBS.

In subsequent studies, the effect of mAb A54 on LPS-induced sepsis, was investigated. C57BL/6 mice (n=8) were treated with A54 mAb (500 μg/mouse) or Roneparstat (SST) (1.2 mg/mouse) or PBS as control, 30 min before LPS injection (15 mg/kg, i.p.). SST was given once again (1.2 mg/mouse) 16 hours after LPS administration. Survival of mice was monitored every 12 h for 8 days (FIG. 10). The results indicate that A54 mAb effectively protects mice from LPS-induced sepsis.

Figure 11A:
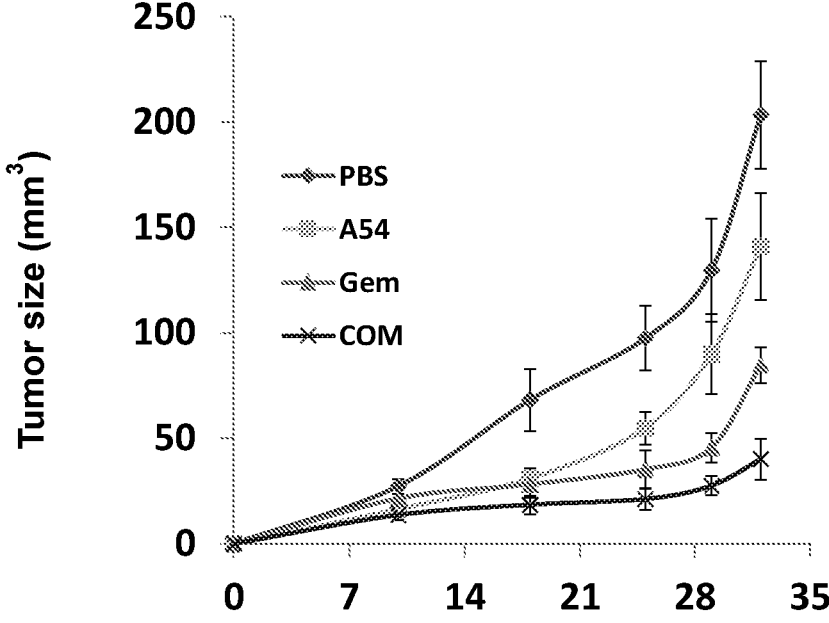
FIG. 11A and FIG. 11B are graphs representing the size
and weight, respectively, of tumors excised from C57BL/6
mice treated with vehicle (PBS), mAb A54, Gemcitabine, or
a combination of mAb A54+Gemcitabine.
Figure 11B:
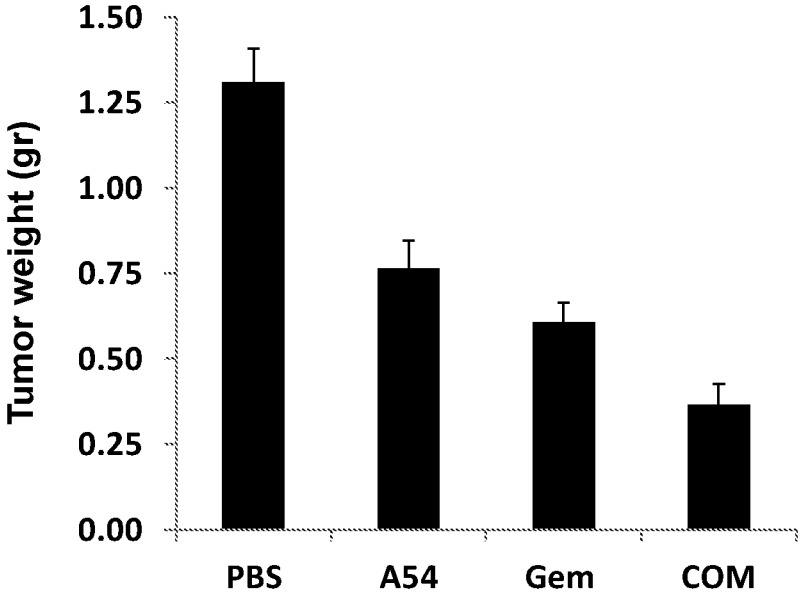
Figure 11C:
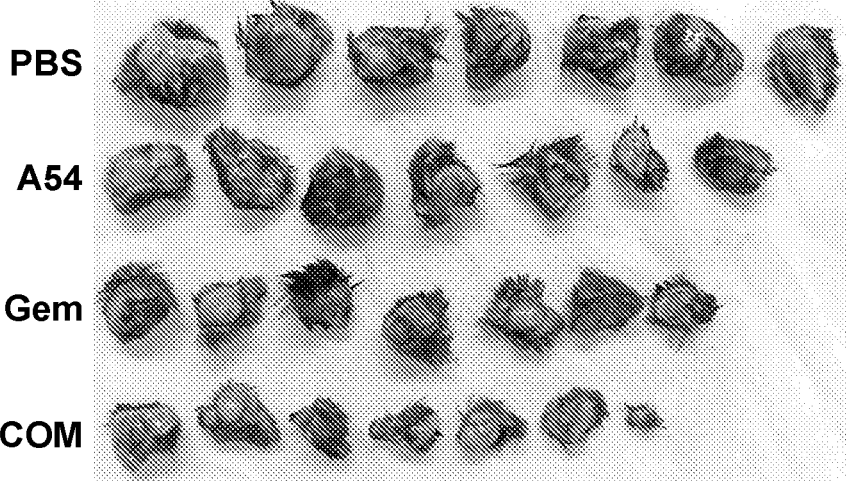
FIG. 11C displays
photographs of the tumors.

Example 11. Combination of A54 mAb and Gemcitabine Attenuates Pancreatic Tumor Growth The effect of mAb A54 on pancreatic tumor growth was investigated. C57BL/6 mice (n=7) were inoculated (s.c.) with Panc02 cells ($1\times10^6$), and mice were treated with A54 mAb (360 μg/mouse, 2 times/week), Gemcitabine (Gem; 30 mg/kg twice a week), A54 mAb+Gemcitabine (as noted) or vehicle alone (PBS) as control. Tumor development was calculated from external caliper tumor measurements (FIG. 11A). At the end of the experiment on day 32, tumors were resected, photographed (FIG. 11C) and weighed (FIG. 11B). The results indicate that treatment of pancreatic cancer by a combination of A54 mAb and Gemcitabine attenuates tumor growth.

Example 12. A54 mAb and Heparanase Interactions

Figure 12A:
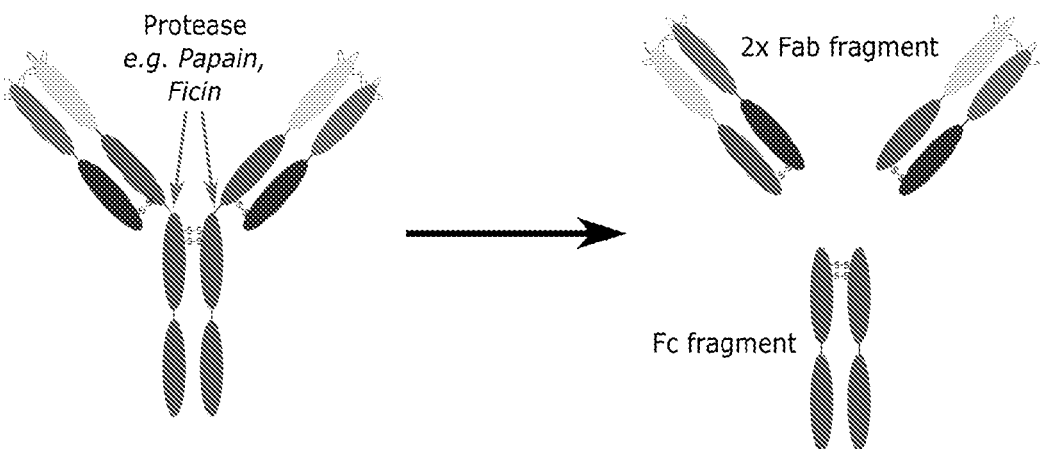
FIG. 12A is a schematic illustration of IgG digestion by
papain and ficin proteases.
Figure 12B:
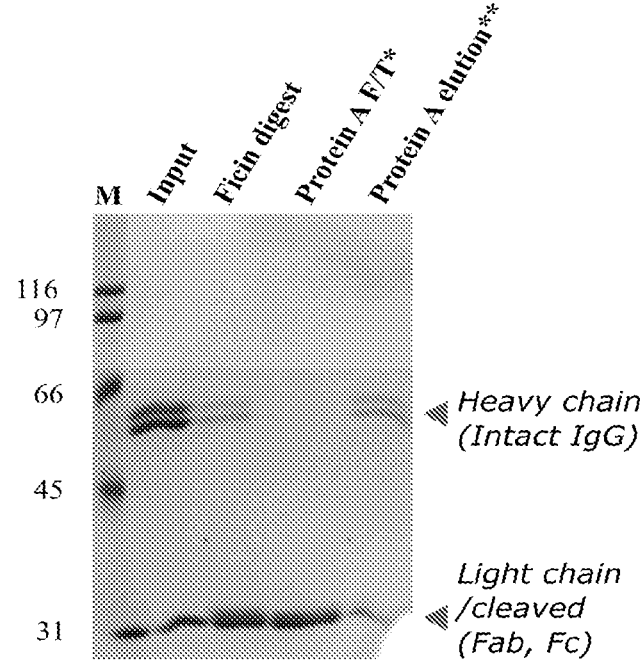
FIG. 12B is an SDS-PAGE gel
showing cleavage and purification of A54 Fab.
Figure 12C:
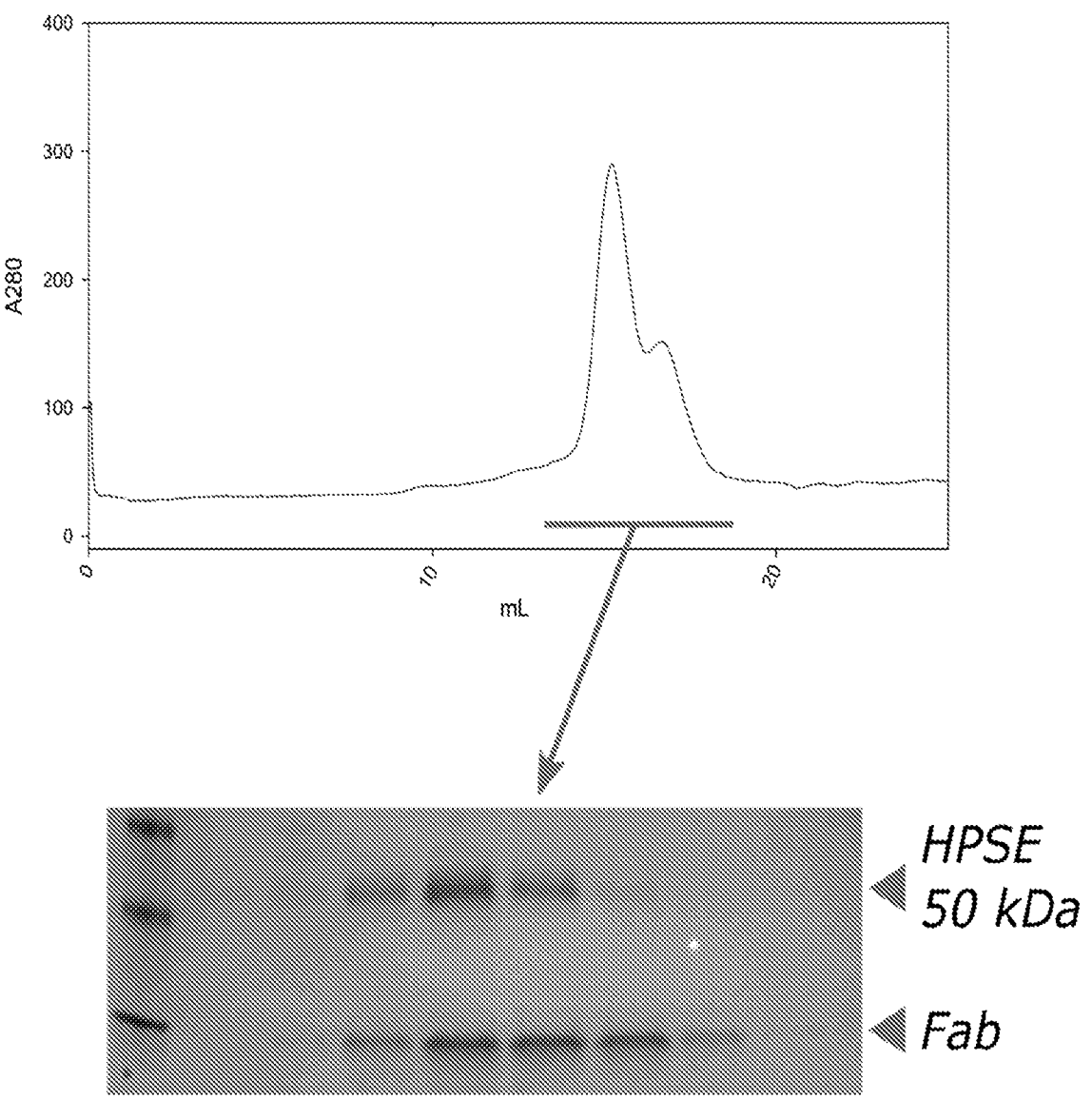
FIG. 12C is
a size exclusion chromatography separation of bound A54-
HPSE complex (main peak) from unbound Fab (righthand
shoulder).

The interactions of A54 mAb and heparanase were investigated by X-ray crystallography. Fab fragments were prepared from intact A54 antibody using the Thermo Scientific mouse IgG1 Fab and F(ab')2 preparation kit and standard manufacturers protocols. The isolated Fab fragments were further purified by size exclusion chromatography to remove contaminants and exchange the buffer into 20 mM HEPES pH 7.4, 200 mM NaCl, 1 mM DTT (FIGS. 12A-12B). Purified A54 was mixed with purified heparanase (=HPSE) at a ~2:1 Fab: HPSE ratio. The mixture was incubated at room temperature for 2 hours, then purified again by size exclusion chromatography to remove unbound Fab fragments (FIG. 12C).

The purified A54+Fab complex was concentrated to 5.4 mg/mL and tested for crystallization using commercially available screens. Crystals were found in the PACT Premier crystallization screen (Molecular Dimensions) condition E5 (0.2 M sodium nitrate, 20% polyethylene glycol 3350). Crystals were transferred to cryoprotectant solution (0.2 M sodium nitrate, 20% polyethylene glycol 3350, 25% ethylene glycol) before harvesting and flash cooling in liquid nitrogen for X-ray data collection.

X-ray diffraction data were collected on beamline I04-1 of the Diamond Light Source UK and processed to 3.54 Å using the XDS2 and STARANISO3 pipelines. The structure was phased by molecular replacement using the structures of unliganded HPSE (PDB accession code 5E8M) and an unrelated mouse IgG Fab fragment (PDB accession code 1AE6). The structure was further improved by iterative rounds of manual model building and maximum-likelihood refinement using COOT and REFMAC5 respectively. Refinement was carried out using TLS restraints, jelly body restraints, and Prosmart restraints using 5E8M and 1AE6 as reference models. The final model was checked using the wwPDB validation server.

The crystallography data indicate that A54 Fab binds to HPSE on the (B/a) 8-barrel domain, right above HBD-II (Gln270-Lys280; FIGS. 14A and 14B). This interaction prevents HPSE from binding its HS substrates by steric occlusion of the enzyme binding cleft (depicted in FIG. 15F). Inspection of protein surface charges shows a major electrostatic contribution to the A54-HPSE interaction. HBD-II is substantially positively charged, whereas the binding interface of A54 is negatively charged (FIG. 14C).

Figure 13:
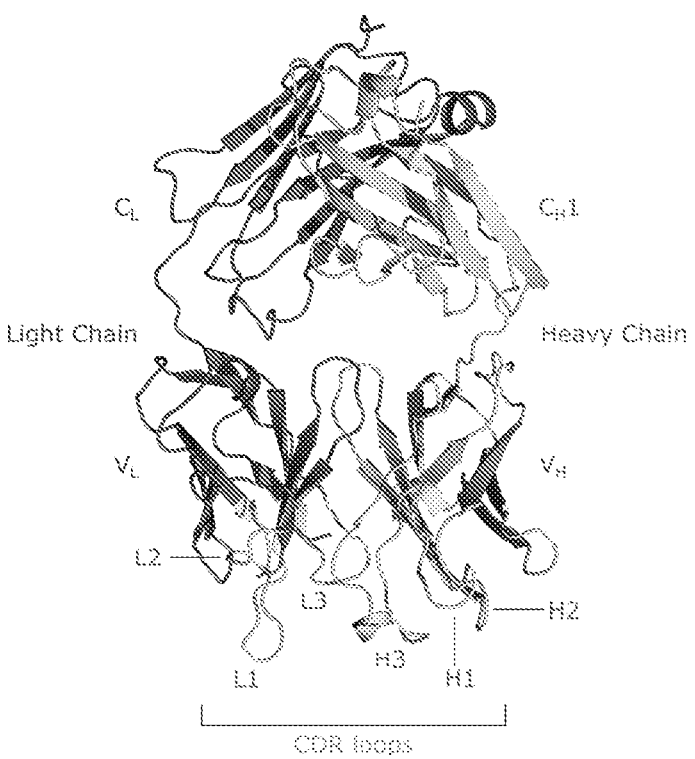
FIG. 13 is a schematic illustration of the tertiary Fab
structure of the A54 CDR loops.

The results show that the single most significant region of HPSE in the A54-HPSE interface is HBD-II. Several negatively charged A54 amino acids (Asp123VH, Asp125VH, Glu78VH, Asp20VL, Glu116VL, Asp117VL) cluster at the A54-HPSE interface, forming a network of salt bridges that strongly stabilize the binding interaction. Cation-x interactions also predominate, involving Tyr124VH and Tyr55VL, which also have a strong charge component. As expected, the CDR loops mediate nearly all the A54-HPSE binding interactions. FIG. 13 is a schematic illustration of the tertiary Fab structure of the A54 CDR loops. Each CDR loop interaction is described in more detail below.

H1 Interactions

The A54 H1 loop does not have any interactions with HPSE.

Figure 15A:
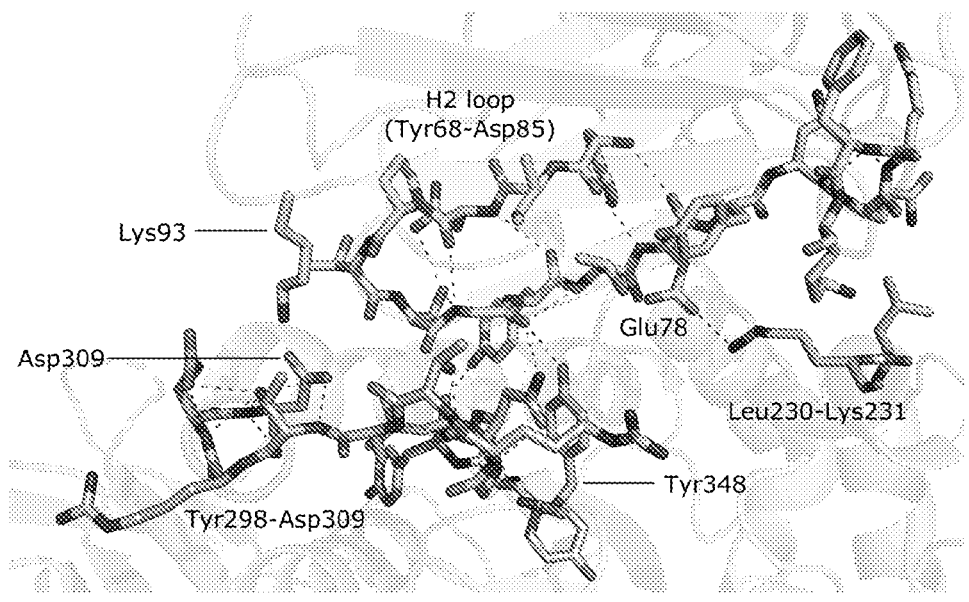
FIG. 15A is a schematic illustration showing the interac-
tions between the A54 H2 loop (green) and HPSE (blue).

H2 Interactions (FIG. 15A)

H2 (Tyr68-Asp85) interacts with the HPSE region around Tyr298-Asp309, as well as some nearby residues (Tyr348, Lys231). A54 Lys93 does not strictly belong to the H2 loop, but it appears close in space to the H2 interactions. Particularly important interactions in this region include salt bridges between $Glu78_{454}$ and $Lys231_{HPSE}$, and between $Lys293_{454}$ and $Asp309_{HPSE}$.

Figure 15B:
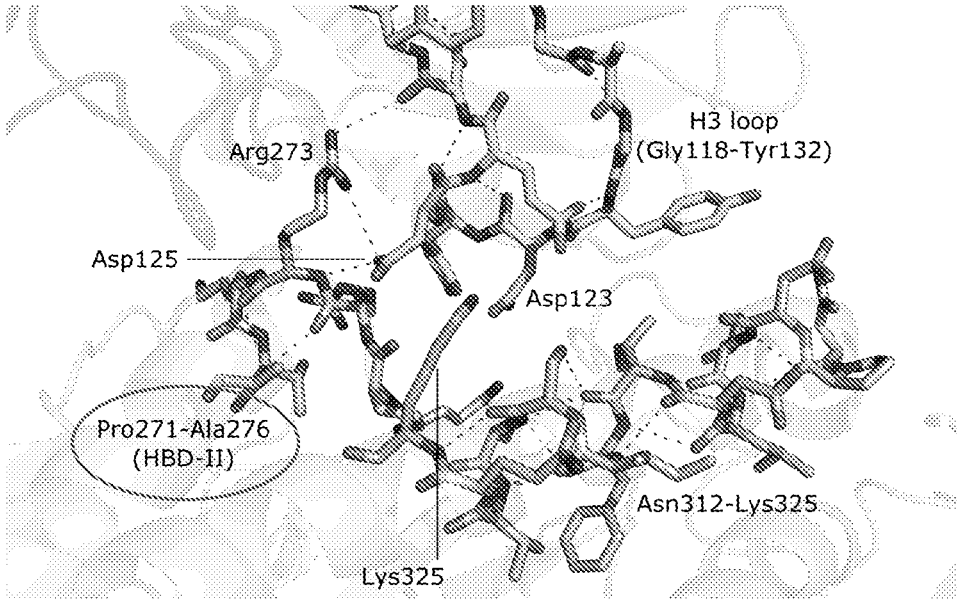
FIG. 15B is a schematic illustration showing the interactions
between the A54 H3 loop (green) and HPSE (blue).

H3 Interactions (FIG. 15B)

H3 (Gly118-Tyr132) interacts with the HPSE α-helix around Asn312-Lys325, and some residues of HBD-II (Pro271-Ala276). There are clear electrostatic interactions between $Asp123_{454}$ and $Lys325_{HPSE}$, as well as $Asp125_{454}$ and $Arg273_{HPSE}$.

Figure 15C:
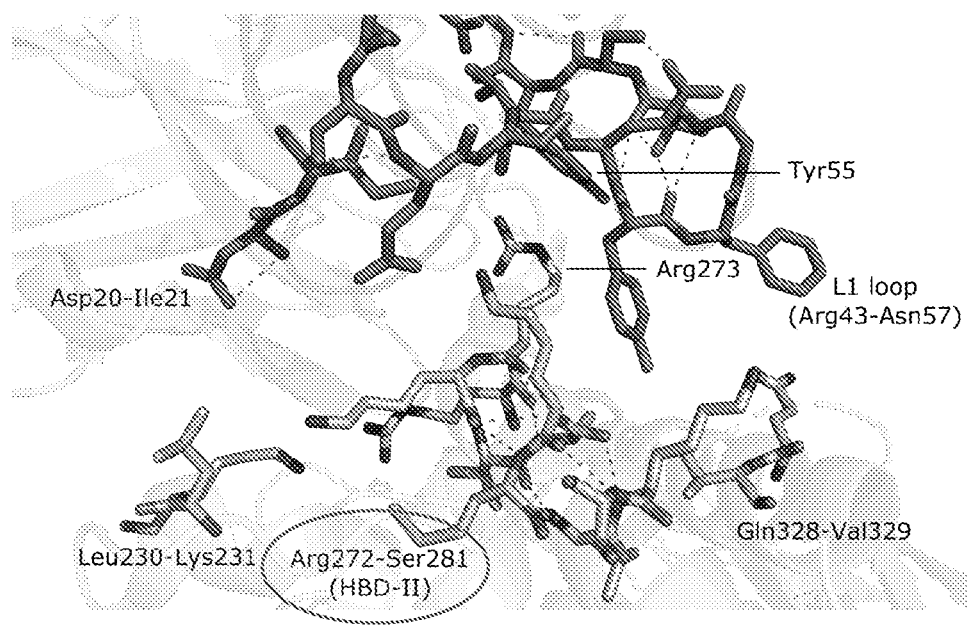
FIG.
15C is a schematic illustration showing the interactions
between the A54 L1 loop (red) and HPSE (blue).

L1 interactions (FIG. 15C)

L1 (Arg43-Asn57) interactions are predominantly with the HBD-II region of HPSE (Arg272-Ser281), as well as some nearby residues. Asp20-Ile21 of A54 are also included, as they lie close to the L1 loop. There are no apparent salt bridges or H-bonds involved in L1 interactions, although Tyr55 is well placed to make a cation-x interaction with Arg273.

L2 Interactions

The A54 L2 loop does not have any interactions with HPSE.

Figure 15D:
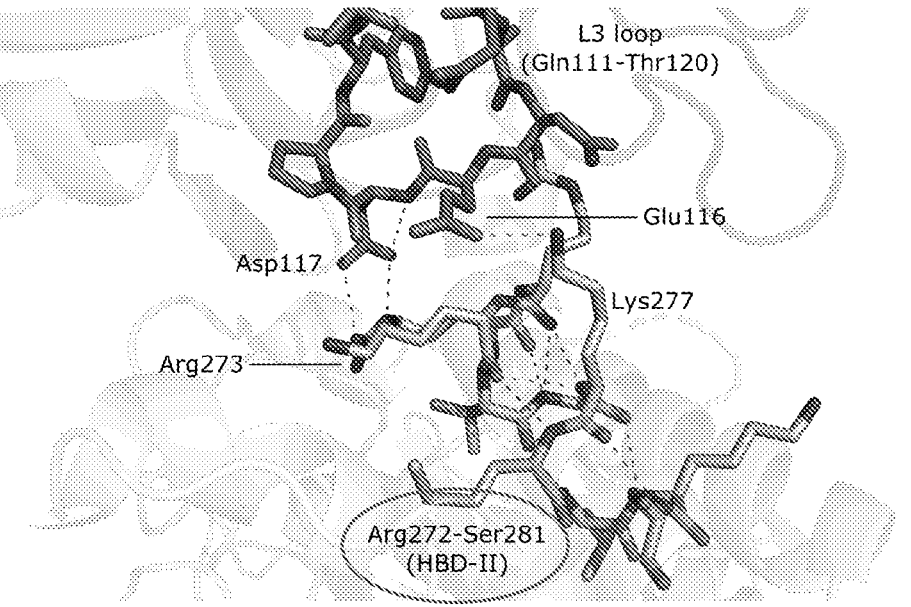
FIG. 15D
is a schematic illustration showing the interactions between
the A54 L3 loop (red) and HPSE (blue).

L3 Interactions (FIG. 15D)

L3 (Gln111-Thr120) interactions are predominantly with the HBD-II region of HPSE (Arg272-Ser281). Important salt bridges are formed between $Glu116_{454}$ and $Lys277_{HPSE}$, and $Asp117_{454}$ and $Arg273_{HPSE}$.

Figure 15E:
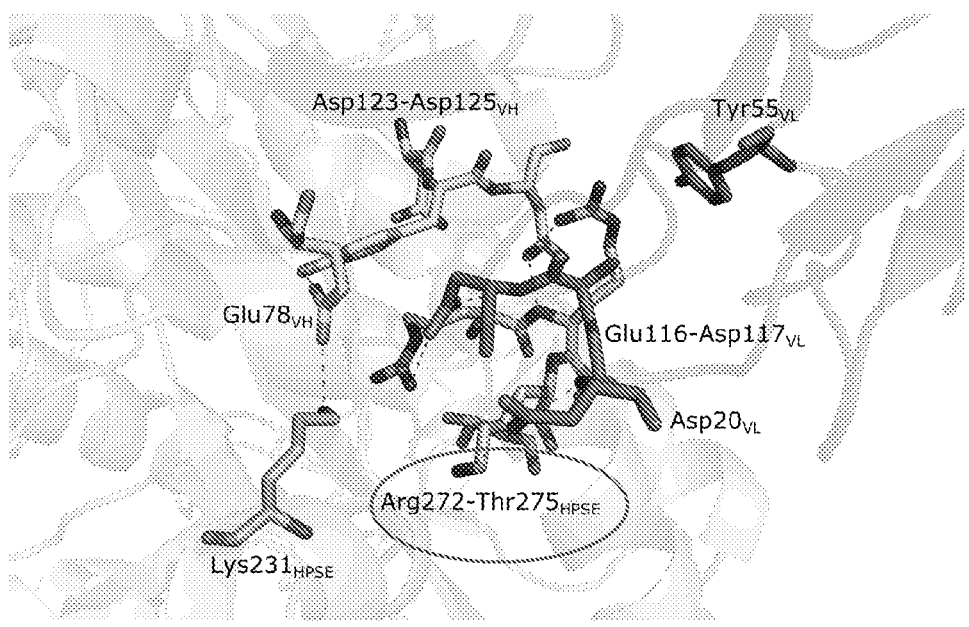
FIG. 15E is a
schematic illustration showing the interactions between
HPSE HBD-II residues (blue), and residues from A54 VH
(green) and VL (red).

FIG. 15E is a schematic illustration showing the interactions between HPSE HBD-II residues (blue), and residues from A54 VH (green) and VL (red).

Figure 15F:
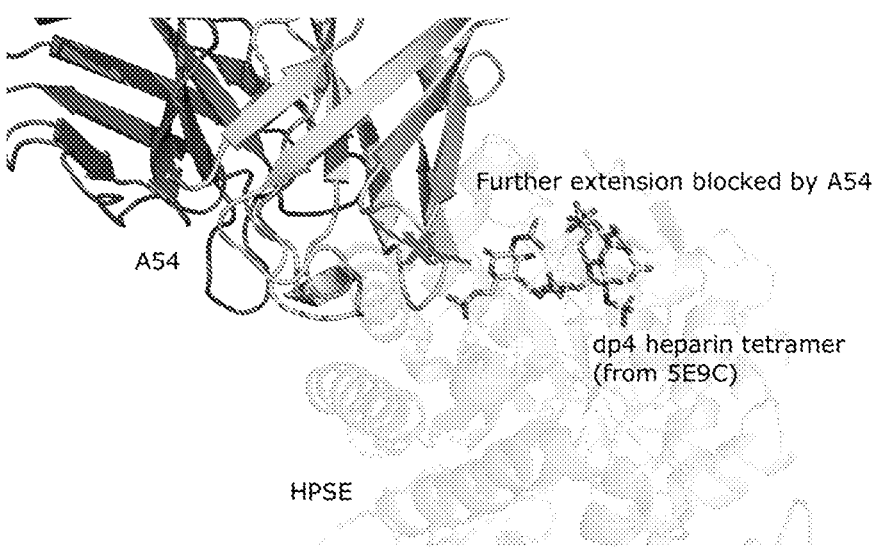
FIG. 15F is a schematic illustration
displaying an overlay of dp4 tetrasaccharide from PDB
5E9C (cyan) with the A54-HPSE complex showing how
A54 sterically occludes the HPSE binding cleft.

FIG. 15F is a schematic illustration displaying an overlay of dp4 tetrasaccharide from PDB 5E9C (cyan) with the A54-HPSE complex showing how A54 sterically occludes the HPSE binding cleft. A54 binds HPSE very near to the position of dp4. Natural HS substrates, which extend beyond the position of dp4, would be sterically blocked from accessing the HPSE active site cleft (red arrow).

Summary of Interactions

Tables 2 and 3 summarize the A54 and HPSE residues involved in the binding interface, as determined by PISA5 analysis. The analysis is broken down by antibody chain: Table 2 presents the heavy chain (VH) interactions, Table 3 presents the light chain (VL) interactions. Some HPSE residues appear in both tables, as they interact with both VH and VL. The HPSE model contains two chains, corresponding to the 50 kDa (A) and 8 kDa (B) chains of the protein. The HPSE residues involved in the binding are from chain A. The A54 residues are grouped according to the CDR loops of the residues. Some A54 interacting residues do not belong to a CDR loop.

Also shown are whether the residues are involved in H-bonding or salt bridge interactions (H/S), estimated accessible/buried surface areas of the interaction (ASA/BSA), and estimated contribution to binding energetics (DeltaG):

1. ASA: Accessible surface area-Area of a monomeric unit, residue or atom, which is accessible to solvent. ASA is measured in square angstroms;

2. BSA: Buried Surface Area-Surface area, which becomes inaccessible to solvent, e.g. at protein folding or in course of interface formation, measured in square angstroms;

3. DeltaG: Solvation energy gain upon interface formation, kcal/mol. Solvation Energy (SE) is the energy difference between bound and unbound states of monomeric units, residues or atoms, which is due to the solvation effect. In bound (interfacing) state, part of structure's surface becomes inaccessible to solvent. If bound surfaces have a positive solvation effect, the total energy decreases upon binding, which is known as the hydrophobic interaction.

TABLE 2

| A54 VL-HPSE interactions | | | | | | |
|---|---|---|---|---|---|---|
| Amino acid | Residue number | H-bond/ Salt bridge? | ASA | BSA | DeltaG | |
| Interfacing residues-A54 | | | | | | |
| H:TYR | 69 | | 34.85 | 1.6 | -0.02 | H2 loop |
| H:ILE | 70 | | 10.7 | 3.18 | 0.05 | |
| H:THR | 73 | | 52.25 | 34.8 | 0.2 | |
| H:THR | 74 | H | 63.46 | 62.96 | 0.27 | |
| H:GLY | 75 | H | 48.27 | 44.65 | 0.13 | |
| H:TYR | 76 | H | 76.32 | 76.05 | 0.22 | |
| H:THR | 77 | H | 49.9 | 10.14 | -0.05 | |
| H:GLU | 78 | S | 81.71 | 52.19 | -0.4 | |
| H:TYR | 79 | | 47.39 | 1.6 | -0.02 | |
| H:GLN | 81 | | 140.64 | 27.9 | -0.29 | |
| H:LYS | 84 | | 110.27 | 43.71 | -0.47 | |
| H:ALA | 91 | | 35.7 | 0.29 | 0 | Not in |
| H:LYS | 93 | HS | 125.29 | 58.57 | -1.07 | CDR loops |
| H:TYR | 122 | | 110.63 | 70.64 | 0.7 | H3 loop |
| H:ASP | 123 | S | 65.43 | 59.03 | -0.27 | |
| H:TYR | 124 | | 83.85 | 65.22 | 0.75 | |
| H:ASP | 125 | HS | 137.18 | 100.86 | -0.28 | |
| H:GLU | 126 | | 71.9 | 18.64 | -0.26 | |
| H:ASP | 127 | H | 20.18 | 10.12 | -0.12 | |
| H:TYR | 128 | | 189.39 | 8.87 | 0.14 | |
| Interfacing residues-HPSE | | | | | | |
| A:LEU | 230 | | 84.91 | 25.55 | 0.41 | |
| A:LYS | 231 | S | 126.88 | 59.98 | 0.43 | |
| A:GLN | 270 | H | 56.36 | 32.2 | -0.22 | |
| A:PRO | 271 | | 20.13 | 12.86 | -0.09 | |
| A:ARG | 272 | | 110.41 | 76.22 | 0.79 | |

TABLE 2-continued

| | | A54 VL-HPSE interactions | | | |
|---|---|---|---|---|---|
| Amino acid | Residue number | H-bond/ Salt bridge? | ASA | BSA | DeltaG |
| A:ARG | 273 | HS | 197.53 | 75.86 | −0.83 |
| A:ALA | 276 | | 21.85 | 1.51 | 0.02 |
| A:TYR | 298 | H | 15.64 | 0.49 | −0.01 |
| A:TYR | 299 | H | 15.55 | 15.55 | −0.17 |
| A:LEU | 300 | | 28.93 | 28.6 | 0.46 |
| A:ASN | 301 | H | 41.87 | 27.94 | −0.04 |
| A:THR | 304 | H | 97.93 | 25.48 | 0.08 |
| A:ALA | 305 | | 16.47 | 1.5 | 0.02 |
| A:THR | 306 | H | 53.39 | 19.25 | 0.31 |
| A:GLU | 308 | | 113.29 | 10.65 | −0.12 |
| A:ASP | 309 | S | 38.28 | 34 | −0.41 |
| A:ASN | 312 | | 50.04 | 9.66 | −0.11 |
| A:ASP | 314 | | 77.37 | 29.64 | 0.17 |
| A:VAL | 315 | | 22.8 | 21.21 | 0.34 |
| A:ILE | 318 | | 77.71 | 61.32 | 0.95 |
| A:SER | 321 | | 45.1 | 13.33 | −0.12 |
| A:SER | 322 | | 13.91 | 12.24 | −0.11 |
| A:LYS | 325 | S | 97.11 | 52.82 | −1.15 |
| A:TYR | 348 | H | 101.7 | 46.39 | −0.04 |

TABLE 3

| | | A54 V$_L$-HPSE interactions | | | | |
|---|---|---|---|---|---|---|
| Amino acid | Residue number | H-bond/ Salt bridge? | ASA | BSA | DeltaG | |
| | | Interfacing residues-A54 V$_L$ | | | | |
| L:ASP | 20 | | 109.76 | 15.25 | −0.14 | Not in |
| L:ILE | 21 | | 0.17 | 0.17 | 0 | CDR loops |
| L:GLU | 46 | | 117.79 | 5.24 | −0.06 | L1 loop |
| L:SER | 47 | | 46.58 | 0.37 | 0 | |
| L:GLU | 49 | | 71.2 | 1.59 | −0.02 | |
| L:TYR | 50 | | 157.02 | 100.71 | 0.69 | |

TABLE 3-continued

| | | A54 V$_L$-HPSE interactions | | | | |
|---|---|---|---|---|---|---|
| Amino acid | Residue number | H-bond/ Salt bridge? | ASA | BSA | DeltaG | |
| L:PHE | 51 | | 201.18 | 6.25 | 0.1 | |
| L:TYR | 55 | | 65.82 | 25.87 | 0.21 | |
| L:SER | 114 | H | 27.53 | 10.36 | −0.12 | L3 loop |
| L:ASN | 115 | | 36.95 | 35.62 | −0.33 | |
| L:GLU | 116 | S | 69.24 | 51.05 | 0.25 | |
| L:ASP | 117 | S | 125.73 | 67.54 | −0.76 | |
| L:PRO | 118 | | 71.47 | 2.34 | 0.04 | |
| L:TYR | 119 | | 121.81 | 4.68 | −0.03 | |
| | | Interfacing residues-HPSE | | | | |
| A:LEU | 230 | | 84.91 | 14.9 | 0.24 | |
| A:LYS | 231 | | 126.88 | 4.69 | 0.07 | |
| A:ARG | 272 | S | 110.41 | 25.87 | −0.09 | |
| A:ARG | 273 | H | 197.53 | 121.67 | −0.43 | |
| A:LYS | 274 | | 71.84 | 49.52 | 0.51 | |
| A:ALA | 276 | | 21.85 | 16.28 | 0.19 | |
| A:LYS | 277 | S | 142.35 | 85.08 | −1.16 | |
| A:LYS | 280 | | 75.86 | 1.51 | 0.02 | |
| A:GLN | 328 | | 121.39 | 5.98 | 0.05 | |
| A:VAL | 329 | | 19.74 | 10.21 | 0.16 | |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for inhibiting or treating a disease or disorder associated with heparanase activity in a subject in need thereof, comprising administering to the subject a therapeutically effective amount of an antibody or an antigen-binding fragment, directed against a heparanase enzyme, wherein the antibody, or antigen-binding fragment comprises six complementarity-determining regions (CDRs), and wherein the six complementarity-determining regions comprise SEQ. ID NO: 1, SEQ. ID NO: 2, SEQ. ID NO: 3, SEQ. ID NO: 4, SEQ. ID NO: 5 and SEQ. ID NO: 6.

2. The method of claim 1, wherein the disease or disorder is a malignant proliferative disease, carcinoma, sarcoma, melanoma, a hematological malignancy, malignant proliferative disease, type 1 diabetes, an inflammatory disorder, a kidney disorder, or a combination thereof.

3. The method of claim 2, comprising inhibiting tumor progression, inhibiting tumor metastasis, or a combination thereof.

4. The method of claim 2, further comprising administering chemotherapy, radiation therapy, or a combination thereof to the subject.

* * * * *

SEQUENCE LISTING

<160> NUMBER OF SEQ ID NOS: 17

<210> SEQ ID NO 1
<211> LENGTH: 6
<212> TYPE: PRT
<213> ORGANISM: Mus musculus

<400> SEQUENCE: 1

Gly Tyr Thr Phe Thr Asn
1               5

<210> SEQ ID NO 2
<211> LENGTH: 17
<212> TYPE: PRT
<213> ORGANISM: Mus musculus

<400> SEQUENCE: 2

Tyr Ile Asn Pro Thr Thr Gly Tyr Thr Glu Tyr Asn Gln Lys Phe Lys
1               5                   10                  15

Asp

<210> SEQ ID NO 3
<211> LENGTH: 15
<212> TYPE: PRT

-continued

<213> ORGANISM: Mus musculus

<400> SEQUENCE: 3

Gly Gly Ala Gly Tyr Asp Tyr Asp Glu Asp Tyr Ala Met Asp Tyr
1               5               10              15

<210> SEQ ID NO 4
<211> LENGTH: 15
<212> TYPE: PRT
<213> ORGANISM: Mus musculus

<400> SEQUENCE: 4

Arg Ala Ser Glu Ser Val Glu Tyr Phe Gly Thr Ser Tyr Met Asn
1               5               10              15

<210> SEQ ID NO 5
<211> LENGTH: 7
<212> TYPE: PRT
<213> ORGANISM: Mus musculus

<400> SEQUENCE: 5

Leu Ala Ser Ile Leu Glu Ser
1               5

<210> SEQ ID NO 6
<211> LENGTH: 9
<212> TYPE: PRT
<213> ORGANISM: Mus musculus

<400> SEQUENCE: 6

Gln Gln Ser Asn Glu Asp Pro Tyr Thr
1               5

<210> SEQ ID NO 7
<211> LENGTH: 124
<212> TYPE: PRT
<213> ORGANISM: Mus musculus

<400> SEQUENCE: 7

Gln Val Gln Leu Gln Gln Ser Gly Ala Glu Leu Ala Lys Pro Gly Ala
1               5               10              15

Ser Val Arg Met Ser Cys Lys Ala Ser Gly Tyr Thr Phe Thr Asn Tyr
            20              25              30

Trp Met His Trp Val Lys Gln Arg Pro Gly Gln Gly Leu Glu Trp Ile
        35              40              45

Gly Tyr Ile Asn Pro Thr Thr Gly Tyr Thr Glu Tyr Asn Gln Lys Phe
    50              55              60

Lys Asp Lys Ala Thr Leu Thr Ala Asp Lys Ser Ser Ser Thr Ala Tyr
65              70              75              80

Met Gln Leu Ser Ser Leu Thr Ser Glu Asp Ser Ala Val Tyr Tyr Cys
            85              90              95

Ala Arg Gly Gly Ala Gly Tyr Asp Tyr Asp Glu Asp Tyr Ala Met Asp
            100             105             110

Tyr Trp Gly Gln Gly Thr Ser Val Thr Val Ser Ser
        115             120

<210> SEQ ID NO 8
<211> LENGTH: 111
<212> TYPE: PRT
<213> ORGANISM: Mus musculus

<400> SEQUENCE: 8

-continued

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Phe
                20                  25                  30

Gly Thr Ser Tyr Met Asn Trp Tyr Gln Gln Lys Pro Gly Gln Pro Pro
            35                  40                  45

Lys Leu Leu Ile Tyr Leu Ala Ser Ile Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110
```

```
<210> SEQ ID NO 9
<211> LENGTH: 371
<212> TYPE: DNA
<213> ORGANISM: Mus musculus

<400> SEQUENCE: 9
caagtgcagc tgcagcagag cggcgccgag ctggccaagc ctggcgcttc tgtgcggatg      60
agctgcaagg cctctggcta caccttcacc aactactgga tgcactgggt caagcagaga     120
cctggacagg gcctggaatg gatcggctac atcaacccca ccaccggcta cacggaatac     180
aaccagaagt tcaaggacaa ggccacactg acagccgaca aaagcagcag caccgcctac     240
atgcagctga gcagcctgac cagcgaggac agcgccgtgt actactgcgc cagaggcgga     300
gccggctatg attacgacga ggattacgcc atggactact ggggccaggg tacaagcgtg     360
accgtgtcca g                                                          371
```

```
<210> SEQ ID NO 10
<211> LENGTH: 333
<212> TYPE: DNA
<213> ORGANISM: Mus musculus

<400> SEQUENCE: 10
gacatcgtgc tgacccagag ccctgcctct ctggccgtgt ccctgggcca gcgggccacc      60
atcagctgca gagccagcga gagcgtggaa tacttcggca ccagctacat gaactggtac     120
cagcagaaac ctggccagcc tcctaagctg ctgatctacc tggctagcat cctggaaagc     180
ggcatccccg ccagattcag cggatctggc agcggcaccg acttcaccct gaacatccac     240
cccgtggaag aggaagatgc cgccacatac tactgccagc aatctaatga ggacccctac     300
accttcggcg gcggaacaaa gctggaaatc aag                                  333
```

```
<210> SEQ ID NO 11
<211> LENGTH: 15
<212> TYPE: DNA
<213> ORGANISM: Mus musculus

<400> SEQUENCE: 11
aactactgga tgcac                                                        15
```

```
<210> SEQ ID NO 12
<211> LENGTH: 51
<212> TYPE: DNA
<213> ORGANISM: Mus musculus
```

-continued

```
<400> SEQUENCE: 12
tacatcaacc ccaccaccgg ctacacggaa tacaaccaga agttcaagga c              51

<210> SEQ ID NO 13
<211> LENGTH: 45
<212> TYPE: DNA
<213> ORGANISM: Mus musculus

<400> SEQUENCE: 13
ggcggagccg gctatgatta cgacgaggat tacgccatgg actac                     45

<210> SEQ ID NO 14
<211> LENGTH: 45
<212> TYPE: DNA
<213> ORGANISM: Mus musculus

<400> SEQUENCE: 14
agagccagcg agagcgtgga atacttcggc accagctaca tgaac                     45

<210> SEQ ID NO 15
<211> LENGTH: 20
<212> TYPE: DNA
<213> ORGANISM: Mus musculus

<400> SEQUENCE: 15
ctggctagca tcctggaaag                                                 20

<210> SEQ ID NO 16
<211> LENGTH: 27
<212> TYPE: DNA
<213> ORGANISM: Mus musculus

<400> SEQUENCE: 16
cagcaatcta atgaggaccc ctacacc                                         27

<210> SEQ ID NO 17
<211> LENGTH: 10
<212> TYPE: PRT
<213> ORGANISM: Mus musculus

<400> SEQUENCE: 17

Gly Tyr Thr Phe Thr Asn Tyr Trp Met His
1               5                   10
```